United States Patent
Lanzavecchia

(10) Patent No.: US 8,685,402 B2
(45) Date of Patent: Apr. 1, 2014

(54) NEUTRALIZING ANTI-INFLUENZA A VIRUS ANTIBODIES AND USES THEREOF

(75) Inventor: Antonio Lanzavecchia, Porza (CH)

(73) Assignee: Institute for Research in Biomedicine, Bellinzona (CH)

(*) Notice: Subject to any disclaimer, the term of this patent is extended or adjusted under 35 U.S.C. 154(b) by 1054 days.

(21) Appl. No.: 12/509,835

(22) Filed: Jul. 27, 2009

(65) Prior Publication Data

US 2010/0086555 A1 Apr. 8, 2010

Related U.S. Application Data

(60) Provisional application No. 61/083,838, filed on Jul. 25, 2008, provisional application No. 61/181,582, filed on May 27, 2009.

(51) Int. Cl.
| | | |
|---|---|---|
| C07K 16/00 | (2006.01) | |
| A61K 39/42 | (2006.01) | |
| C07H 21/00 | (2006.01) | |
| C12N 5/00 | (2006.01) | |
| C12N 15/00 | (2006.01) | |

(52) U.S. Cl.
USPC .......... 424/147.1; 424/133.1; 424/135.1; 530/387.3; 530/388.1; 530/388.15; 530/388.3; 536/23.1; 536/23.53; 435/320.1; 435/325

(58) Field of Classification Search
None
See application file for complete search history.

(56) References Cited

U.S. PATENT DOCUMENTS

| | | | |
|---|---|---|---|
| 3,766,162 | A | 10/1973 | Spector |
| 3,791,932 | A | 2/1974 | Schuurs et al. |
| 3,817,837 | A | 6/1974 | Rubenstein et al. |
| 4,179,337 | A | 12/1979 | Davis |
| 4,233,402 | A | 11/1980 | Maggio et al. |
| 4,495,285 | A | 1/1985 | Shimizu |
| 4,609,546 | A | 9/1986 | Hiratani |
| 4,676,980 | A | 6/1987 | Segal |
| 4,766,106 | A | 8/1988 | Katre et al. |
| 4,831,175 | A | 5/1989 | Gansow |
| 5,595,721 | A | 1/1997 | Kaminski et al. |
| 6,300,064 | B1 | 10/2001 | Knappik et al. |

FOREIGN PATENT DOCUMENTS

| | | |
|---|---|---|
| EP | 1264885 | 12/2002 |
| EP | 1925318 | 5/2008 |
| WO | 0052031 | 9/2000 |
| WO | 0052473 | 9/2000 |
| WO | 2006124269 | 11/2006 |
| WO | 2007045477 | 4/2007 |
| WO | 2007134327 | 11/2007 |
| WO | 2008028946 | 3/2008 |
| WO | 2008054606 | 5/2008 |
| WO | 2008066691 | 6/2008 |
| WO | 2008076379 | 6/2008 |
| WO | 2008084410 | 7/2008 |
| WO | 2008110937 | 9/2008 |

OTHER PUBLICATIONS

Corbeil et al 1996 Vaccine vol. 14, pp. 521-525.*
Paul Fundamental Immunology $3^{rd}$ 1993, pp. 242, 292-295.*
Rudikoff PNAS vol. 79 pp. 1979-9183 1982.*
Coleman Reasearch Immunology 1994 vol. 145, pp. 33-36.*
Casset Biochem Biophys Research Com 2003, vol. 307, pp. 198-205.*
Smirnov et al. Arch Virol 2000 vol. 145, pp. 1733-1741.*
Sigal et al., The Journal of Immunology 1987 vol. 139, pp. 1985-1990.*
Hanson et al., Respiratory Research 2006 vol. 7:126, no pages used in citation.*
Knight et al., Human Antibodies Hybridomas 1992 vol. 3, p. 192 (abstract only).*
Cho et al., "An oriP expression vector containing the HIV-1 Tat/TAR transactivation axis produces high levels of protein expression in mammalian cells," Cytotechnology 2001, 37:23-30.
Cho et al., "Versatile Expression System for Rapid and Stable Production of Recombinant Proteins," Biotechnol Prog 2003, 19:229-232.
Ekiert et al., (2009). "Antibody Recognition of a Highly Conserved Influenza Virus Epitope," Science 324:246-251.
Gabizon et al., (1982). "Liposomes as in Vivo Carriers of Adriamycin: Reduced Cardiac Uptake and Preserved Antitumor Activity in Mice," Cancer Research 42: 4734-4739.
Gerhard et al., (2006). "Prospects for Universal Influenza Virus Vaccine," Emerging Infectious Diseases 12:569-574.
Gioia et al., (2008) "Cross-subtype Immunity Against Avian Influenza in Persons Recently Vaccinated for Influenza," Emerging Infectious Diseases 14:121-128.
Holt et al., "Domain antibodies: proteins for therapy," Trends in Biotechnology 2003, 21(11):484-490.
Jones et al., "High-Level Expression of Recombinant IgG in the Human Cell Line PER.C6," Biotechnol Prog 2003, 19 (1):163-168.
Kashyap et al., (2008). "Combinatorial antibody libraries from survivors of the Turkish H5N1 avian influenza outbreak reveal virus neutralization strategies," Proc. Natl. Acad. Sci. USA 105:5986-5991.

(Continued)

*Primary Examiner* — Zachariah Lucas
*Assistant Examiner* — Myron Hill
(74) *Attorney, Agent, or Firm* — Dennis A. Bennett; Suman Mirmira

(57) ABSTRACT

The invention relates to antibodies and antigen binding fragments thereof, that bind to hemagglutinin and neutralize infection of at least two different group 1 subtypes or at least two different group 2 subtypes of influenza A virus. The invention also relates to nucleic acids that encode, immortalized B cells and cultured single plasma cells that produce, and to epitopes that bind to, such antibodies and antibody fragments. In addition, the invention relates to the use of the antibodies, antibody fragments, and epitopes in screening methods as well as in the diagnosis, treatment and prevention of influenza A virus infection.

14 Claims, 1 Drawing Sheet

(56) References Cited

OTHER PUBLICATIONS

Little et al., "Of mice and men: hybridoma and recombinant antibodies," Immunology Today 2000, 21(8):364-370.

Okuno et al., (1993). "A Common Neutralizing Epitope Conserved between the Hemagglutinins of Influenza A Virus Hi and H2 Strains," Journal of Virology 67:2552-2558.

Prabhu et al., (2009). "Monoclonal Antibodies against the Fusion Peptide of Hemagglutinin Protect Mice from Lethal Influenza A Virus H5N1 Infection," Journal of Virology 83:2553-2562.

Rowe et al., (1999). "Detection of Antibody to Avian Influenza A (H5N1) Virus in Human Serum by Using a Combination of Serologic Assays," J Clin Microbiol 37(4):937-943.

Smirnov et al., (1999). "An Epitope Shared by the Hemagglutinins of H1, H2, H5, and H6 Subtypes of influenza A Virus," Acta Virol 43:237-244.

Smirnov et al., (2000). "Prevention and treatment of bronchopneumonia in mice caused by mouse-adapted variant of avian H5N2 influenza A virus using monoclonal antibody against conserved epitope in the HA stem region," Arch Virol 145:1733-1741.

Sui et al., (2009). "Structural and functional bases for broad-spectrum neutralization of avian and human influenza A viruses," Nature Structural & Molecular Biology 16:265-273.

Temperton, et al., (2005). "Longitudinally Profiling Neutralizing Antibody Response to SARS Coronavirus with Pseudotypes," Emerg Infect Dis 11:411-416.

Throsby et al., (2008). "Heterosubtypic Neutralizing Monoclonal Antibodies Cross-Protective against H5N1 and H1N1 Recovered from Human IgM+ Memory B Cells," PLoS One vol. 3, e3942.

Traggiai et al., (2004). "Heterosubtypic Neutralizing Monoclonal Antibodies Cross-Protective against H5N1 and H1N1 Recovered from Human IgM+ Memory B Cells," Nat Med 10:871-875.

Wrammert et al., (2008). "Rapid cloning of high-affinity human monoclonal antibodies against influenza virus," Nature 453:667-671.

Yoshida et al., (2009). "Cross-Protective Potential of a Novel Monoclonal Antibody Directed against Antigenic Site B of the Hemagglutinin of Influenza A Viruses," PLoS Pathog. vol. 5, e1000350.

Ziegler et al., "Type- and Subtype-Specific Detection of Influenza Viruses in Clinical Specimens by Rapid Culture Assay," Journal of Clinical Microbiology,1995, 33:318-321.

Written Opinion of the International Searching Authority received in International Application No. PCT/IB2009/006616.

Written Opinion of the International Searching Authority received in International Application No. PCT/IB2009/006623.

* cited by examiner

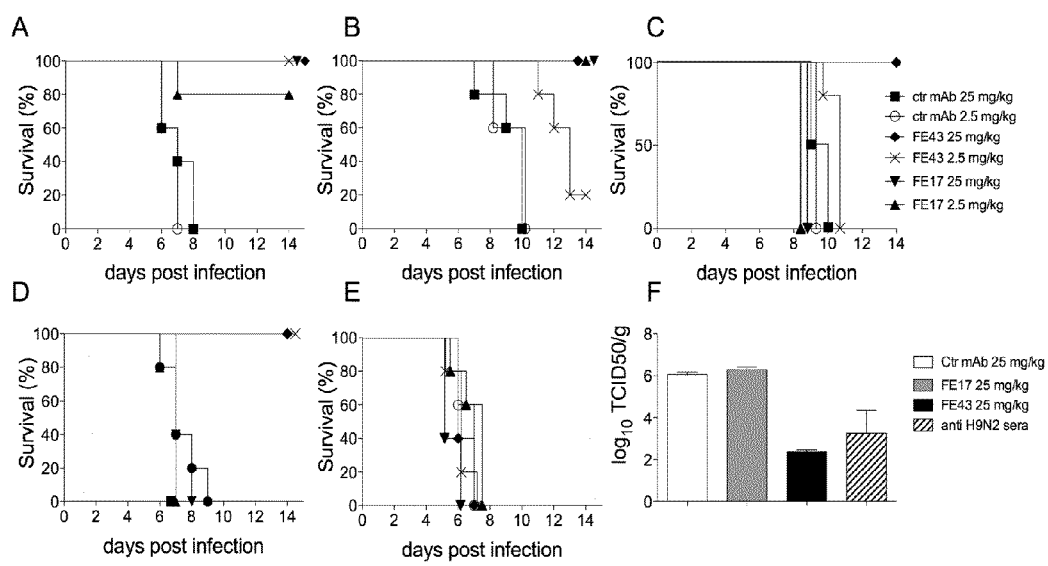

NEUTRALIZING ANTI-INFLUENZA A VIRUS ANTIBODIES AND USES THEREOF

This application claims the benefit of priority of U.S. provisional Application Nos. 61/083,838 and 61/181,582, filed Jul. 25, 2008, and May 27, 2009, respectively, the disclosures of which are hereby incorporated by reference as if written herein in their entirety.

BACKGROUND

The neutralizing antibody response to Influenza A virus is thought to be specific for a given viral subtype. There are 16 influenza A subtypes defined by their hemagglutinins (HA). The 16 HAs, H1-H16, can be classified into two groups. Group 1 consists of H1, H2, H5, H6, H8, H9, H11, H12, H13, and H16 subtypes, and group 2 includes H3, H4, H7, H10, H14 and H15 subtypes. While all subtypes are present in birds, mostly H1, H2 and H3 subtypes cause disease in humans. H5, H7 and H9 subtypes are causing sporadic severe infections in humans and may generate a new pandemic. H1 and H3 viruses continuously evolve generating new variants, a phenomenon called antigenic drift. As a consequence, antibodies produced in response to past viruses are poorly or non protective against new drifted viruses. A consequence is that a new vaccine has to be produced every year against H1 and H3 viruses that are predicted to emerge, a process that is very costly as well as not always efficient. The same applies to the production of a H5 influenza vaccine. Indeed it is not clear whether the current H5 vaccines based on the Vietnam or Indonesia influenza A virus isolates will protect against a future pandemic H5 virus.

For these reasons it would be highly desirable to have a vaccine that induces broadly neutralizing antibodies capable of neutralizing all influenza A virus subtypes as well as their yearly variants (reviewed by Gerhard et al., 2006). In addition broadly neutralizing heterosubtypic antibodies could be used in preventive or therapeutic settings.

Antibodies that recognize influenza A virus have been characterized. Antibodies to M2 (an invariant small protein expressed on infected cells but not on infectious viruses) have shown some protective effect in vivo, possibly by targeting infected cells for destruction by NK cells or cytotoxic T cells. However, the HA is the primary target of neutralizing antibodies. It comprises a large ectodomain of ≈500 amino acids that is cleaved by host-derived enzymes to generate 2 polypeptides that remain linked by a disulfide bond. The larger N-terminal fragment (HA1, 320-330 amino acids) forms a membrane-distal globular domain that contains the receptor-binding site and most determinants recognized by virus-neutralizing antibodies. The smaller C-terminal portion (HA2, ≈180 amino acids) forms a stem-like structure that anchors the globular domain to the cellular or viral membrane. The degree of sequence homology between subtypes is smaller in the HA1 polypeptides (34%-59% homology between subtypes) than in the HA2 polypeptide (51%-80% homology). The most conserved region is the sequence around the cleavage site, particularly the HA2 N-terminal 11 amino acids, termed fusion peptide, which is conserved among all influenza A virus subtypes. Part of this region is exposed as a surface loop in the HA precursor molecule (HA0), but becomes inaccessible when HA0 is cleaved into HA1/HA2. In summary there are conserved regions among different HA subtypes especially in the HA1-HA2 joining region and in the HA2 region. However these regions may be poorly accessible to neutralizing antibodies.

There has only been limited success in identifying antibodies that neutralize more than one subtype of influenza A virus and their breath of neutralization is narrow and their potency is low. Okuno et al, (1993) immunized mice with influenza virus A/Okuda/57 (H2N2) and isolated a monoclonal antibody (C179) that binds to a conserved conformational epitope in HA2 and neutralizes the group 1 H2, H1 and H5 subtype influenza A viruses in vitro and in vivo in animal models (Okuno et al., 1993; Smirnov et al., 2000; Smirnov et al., 1999).

Recently Gioia et al., described the presence of H5N1 virus neutralizing antibodies in the serum of some individuals that received a conventional seasonal influenza vaccine (Gioia et al., 2008). The authors suggest that the neutralizing activity might be due to antibodies to neuraminidase (N1). However, monoclonal antibodies were not isolated and target epitopes were not characterized. It is not clear whether the serum antibodies neutralize other subtypes of influenza A virus.

Despite decades of research, there are no marketed antibodies that broadly neutralize or inhibit influenza A virus infection or attenuate disease caused by influenza A virus. Therefore, there is a need to identify new antibodies that protect again multiple subtypes of influenza A virus.

SUMMARY OF THE INVENTION

The invention is based, in part, on the isolation from individuals vaccinated with the seasonal influenza vaccine of naturally occurring human monoclonal antibodies that bind to HA and neutralize infection of more than one subtype of influenza A virus, as well as novel epitopes to which the antibodies of the invention bind. Accordingly, in one aspect of the invention, the invention comprises an antibody and antigen binding fragments thereof that neutralize infection of more than one subtype of influenza A virus, selected from group 1 or group 2 subtypes.

In one embodiment of the invention, the invention comprises an antibody, or an antigen binding fragment thereof, that neutralizes infection of at least two different group 1 subtypes or at least two different group 2 subtypes of influenza A virus. In another embodiment of the invention, the invention comprises an antibody, or an antigen binding fragment thereof, comprising at least one complementarity determining region (CDR) sequence having at least 95% sequence identity to any one of SEQ ID NOs: 1-6, 17-22, 33-38, 49-53, 64-68, 78-82, 93-98, 109-114, 125-127, or 133-135, wherein the antibody neutralizes influenza A virus.

In yet another embodiment of the invention, the invention comprises a heavy chain CDR1 selected from the group consisting of SEQ ID NO: 1, SEQ ID NO: 17, SEQ ID NO: 33, SEQ ID NO: 49, SEQ ID NO: 64, SEQ ID NO: 78, SEQ ID NO: 93, SEQ ID NO: 109, SEQ ID NO: 125 and SEQ ID NO: 133; a heavy chain CDR2 selected from the group consisting of SEQ ID NO: 2, SEQ ID NO: 18, SEQ ID NO: 34, SEQ ID NO: 50, SEQ ID NO: 65, SEQ ID NO: 79, SEQ ID NO: 94, SEQ ID NO: 110, SEQ ID NO: 126 and SEQ ID NO: 134; and a heavy chain CDR3 selected from the group consisting of SEQ ID NO: 3, SEQ ID NO: 19, SEQ ID NO: 35, SEQ ID NO: 51, SEQ ID NO: 66, SEQ ID NO: 80, SEQ ID NO: 95, SEQ ID NO: 111, SEQ ID NO: 127 and SEQ ID NO: 135, wherein the antibody neutralizes influenza A virus. In yet another embodiment of the invention, the invention comprises an antibody, or an antigen binding fragment thereof, comprising a light chain CDR1 selected from the group consisting of SEQ ID NO: 4, SEQ ID NO: 20, SEQ ID NO: 36, SEQ ID NO: 52, SEQ ID NO: 81, SEQ ID NO: 96, and SEQ ID NO: 112; a light chain CDR2 selected from the group consisting of SEQ ID NO: 5, SEQ ID NO: 21, SEQ ID NO: 37, SEQ ID NO: 67, SEQ ID NO: 97, and SEQ ID NO: 113; and a light chain CDR3 selected from the group consisting of SEQ ID NO: 6, SEQ ID NO: 22, SEQ ID NO: 38, SEQ ID NO: 53, SEQ ID NO: 68, SEQ ID NO: 82, SEQ ID NO: 98, and SEQ ID NO: 114, wherein the antibody neutralizes influenza A virus.

In still another embodiment of the invention, the invention comprises an antibody, or an antigen binding fragment thereof, wherein the antibody comprises a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 45 and a light chain variable region comprising the amino acid sequence of SEQ ID NO: 46; or a heavy chain variable region comprising the amino acid sequence of SEQ ID NO: 60 and a light chain variable region comprising the amino acid sequence of SEQ ID NO: 61; or a heavy chain variable region comprising the amino acid sequence of SEQ ID NO: 74 and a light chain variable region comprising the amino acid sequence of SEQ ID NO: 75; or a heavy chain variable region comprising the amino acid sequence of SEQ ID NO: 89 and a light chain variable region comprising the amino acid sequence of SEQ ID NO: 90; or a heavy chain variable region comprising the amino acid sequence of SEQ ID NO: 105 and a light chain variable region comprising the amino acid sequence of SEQ ID NO: 106; or a heavy chain variable region comprising the amino acid sequence of SEQ ID NO: 121 and a light chain variable region comprising the amino acid sequence of SEQ ID NO: 122, and wherein the antibody neutralizes influenza A virus.

In yet another embodiment of the invention, the invention comprises an antibody, or antigen binding fragment thereof, expressed by immortalized B cell clone FB54, FB139, FC6, FC41, FE43, FE53, FE17, FB75, FB 110, FB177, FB79, FC1c, FB118, FB179, FB186, FE9b, FE25, FE54, FG20, FB15b, or FC54, wherein the antibody neutralizes influenza A virus.

In another aspect, the invention comprises a nucleic acid molecule comprising a polynucleotide encoding an antibody or antibody fragment of the invention. In yet another aspect, the invention comprises a vector comprising a nucleic acid molecule of the invention or a cell expressing an antibody of the invention or an antigen binding fragment thereof. In still another aspect, the invention comprises an isolated or purified immunogenic polypeptide comprising an epitope that binds to an antibody or antigen binding fragment of the invention.

The invention further comprises a pharmaceutical composition comprising an antibody of the invention or an antigen binding fragment thereof, a nucleic acid molecule of the invention, a vector comprising a nucleic acid molecule of the invention, a cell expressing an antibody or an antibody fragment of the invention, or an immunogenic polypeptide of the invention, and a pharmaceutically acceptable diluent or carrier. The invention also comprises a pharmaceutical composition comprising a first antibody or an antigen binding fragment thereof, and a second antibody, or an antigen binding fragment thereof, wherein the first antibody is an antibody of the invention, and the second antibody is an antibody, or an antigen binding fragment thereof, that neutralizes influenza A virus infection.

Use of an antibody of the invention, or an antigen binding fragment thereof, a nucleic acid of the invention, a vector comprising a nucleic acid of the invention, a cell expressing a vector of the invention, an isolated or purified immunogenic polypeptide comprising an epitope that binds to an antibody or antibody fragment of the invention, or a pharmaceutical composition of the invention (i) in the manufacture of a medicament for the treatment of influenza A virus infection, (ii) in a vaccine, or (iii) in diagnosis of influenza A virus infection is also contemplated to be within the scope of the invention. Further, use of an antibody of the invention, or an antigen binding fragment thereof, for monitoring the quality of anti-influenza A virus vaccines by checking that the antigen of said vaccine contains the specific epitope in the correct conformation is also contemplated to be within the scope of the invention.

In another aspect, the invention comprises a method of reducing influenza A virus infection or lowering the risk of influenza A virus infection comprising administering to a subject in need thereof, a therapeutically effective amount of an antibody or an antigen binding fragment of the invention.

In a further aspect, the invention comprises an epitope which specifically binds to an antibody of the invention, or an antigen binding fragment thereof, for use (i) in therapy, (ii) in the manufacture of a medicament for treating influenza A virus infection, (iii) as a vaccine, or (iv) in screening for ligands able to neutralize influenza A virus infection.

BRIEF DESCRIPTION OF FIGURES

FIG. 1A-E shows survival plots of mice treated prophylactically with antibodies FE17 or FE43 and challenged 24 hours later with H1N1 A/PR/8/34, H6N1 A/teal/HK/W312/97, H5N1 A/VN/1203/04, H5N1 A/INDO/5/05, or H7N7 A/NL/219/03, respectively.

FIG. 1F shows the results of in vivo neutralizing activity against the non-lethal H9N2 A/ck/HK/G9/97 virus. Mice were injected i.p. either with FE43, FE17, a control antibody or a ferret hyper-immune serum and challenged 24 hours later with $10^5$ TCID50 of the H9N2 virus. Shown are virus titers in the lung at day 4 post-infection.

DETAILED DESCRIPTION OF THE INVENTION

The invention is based, in part, on the discovery and isolation, from individuals that were vaccinated with the seasonal influenza A vaccine, of naturally occurring human antibodies that broadly neutralize influenza A virus of different subtypes. Such antibodies are desirable, as only one or few antibodies are required in order to neutralize different subtypes of influenza A virus. In addition, the epitopes recognized by such antibodies may be part of a vaccine capable of inducing broad protection against both seasonal and candidate pandemic isolates of different influenza A virus subtypes.

Accordingly, in one aspect, the invention provides an antibody and antigen binding fragments thereof that neutralize at least two influenza A viruses in group 1 or group 2 subtypes. In one embodiment, the invention provides an antibody, or an antigen binding fragment thereof, that neutralizes infection of two different group 1 subtypes or two different group 2 subtypes of influenza A virus.

In another aspect of the invention, it provides a neutralizing antibody and antigen binding fragments thereof having broad specificity against HA of different influenza A virus subtypes. In one embodiment, the antibody, or antigen binding fragments of the invention specifically binds to an epitope in the stem region of HA that is conserved among two or more influenza A virus group 1 or group 2 subtypes. In another embodiment, the antibody, or antigen binding fragments of the invention specifically binds to an epitope in the globular head region of HA that is conserved among two or more influenza A virus group 1 or group 2 subtypes.

Human monoclonal antibodies, the immortalized B cell clones or the transfected cells that secrete antibodies of the invention, and nucleic acid encoding the antibodies of the invention are also included within the scope of the invention.

As used herein, the terms "antigen binding fragment," "fragment," and "antibody fragment" are used interchangeably to refer to any fragment of an antibody of the invention that retains the antigen-binding activity of the antibody. Exemplary antibody fragments include, but are not limited to, a single chain antibody, Fab, Fab', F(ab')2, Fv or scFv. The term "antibody" as used herein includes both antibodies and antigen binding fragments thereof.

As used herein, the term "broad specificity" is used to refer to an antibody or an antigen binding fragment of the invention that can bind and/or neutralize two or more group 1 subtypes or two or more group 2 subtypes of influenza A virus.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used, alone or in combination, as prophylactic or therapeutic agents upon appropriate formulation, in association with active vaccination, as a diagnostic tool, or as a production tool as described herein.

The antibody, or antigen binding fragments, of the invention neutralizes more than one subtype of influenza A virus from the group 1 subtypes (H1, H2, H5, H6, H8, H9, H11, H12, H13, and H16 and their variants) or more than one subtype of influenza A virus from the group 2 subtypes (H3, H4, H7, H10, H14 and H15 and their variants). In one embodiment, the antibody of the invention neutralizes more than one subtype of influenza A virus from the group 1 and group 2 subtypes.

The antibody and antibody fragment of the invention is capable of neutralizing various combinations of influenza A virus subtypes. In one embodiment, the antibody can neutralize influenza A virus H1 and H2 subtypes, or H1 and H5 subtypes, or H1 and H9 subtypes, or H2 and H5 subtypes, or H2 and H9 subtypes, or H5 and H9 subtypes, or H3 and H7 subtypes, or H1, H2 and H5 subtypes, or H1, H2 and H9 subtypes, or H1, H5, and H9 subtypes, or H2, H5 and H9 subtypes, or H1, H2, H5 and H9 subtypes. In one embodiment, the antibody and antigen binding fragments of the invention neutralize one or more of the above combinations in addition to neutralizing influenza A virus H6 subtype.

The antibody and antigen binding fragment of the invention have high neutralizing potency. The concentration of the antibody of the invention required for 50% neutralization of influenza A virus can, for example, be about 50 µg/ml or less. In one embodiment, the concentration of the antibody of the invention required for 50% neutralization of influenza A virus is about 50, 45, 40, 35, 30, 25, 20, 17.5, 15, 12.5, 11, 10, 9, 8, 7, 6, 5, 4.5, 4, 3.5, 3, 2.5, 2, 1.5 or about 1 µg/ml or less. In another embodiment, the concentration of the antibody of the invention required for 50% neutralization of influenza A virus is about 0.9, 0.8, 0.75, 0.7, 0.65, 0.6, 0.55, 0.5, 0.45, 0.4, 0.35, 0.3, 0.25, 0.2, 0.15, 0.1, 0.075, 0.05, 0.04, 0.03, 0.02, 0.01, 0.008, 0.006, 0.004, 0.003, 0.002 or about 0.001 µg/ml or less. This means that only low concentrations of antibody are required for 50% neutralization of influenza A. Specificity and potency can be measured using a standard neutralization assay as known to one of skill in the art.

Antibodies of the Invention

The invention provides an antibody having particularly broad specificity to HA and that neutralizes more than one influenza A virus subtype from group 1 or more than one influenza A virus subtype from group 2. The antibody of the invention binds to an epitope in a region of HA that is conserved among two or more influenza A virus group 1 subtypes or among two or more influenza A virus group 2 subtypes.

In one embodiment, the invention provides an antibody that binds to an epitope in the stem region of HA that is conserved among two or more group 1 or group 2 influenza A virus subtypes. In another embodiment, the invention provides an antibody that binds to an epitope in the globular head region of HA that is conserved among two or more group 1 or group 2 influenza A virus subtypes.

In yet another embodiment, the invention provides an antibody, e.g., an isolated antibody or a purified antibody, that specifically binds to a conserved epitope in the stem region or globular head region of HA, and interferes with viral replication or spreading. The invention also provides an antibody, e.g., an isolated antibody or a purified antibody, that specifically binds to a conserved epitope in the stem region or globular head region of HA, and inhibits virus entry into a cell. Without being bound to any theory, in an exemplary embodiment the antibody or antigen binding fragments of the invention bind to a conserved epitope in the stem region of influenza A virus and inhibit virus entry into a cell by interfering with the fusion step. An epitope or antigenic determinant of a protein corresponds to those parts of the molecule that are specifically recognized by the binding site (or paratope) of an antibody. Epitopes are thus relational entities that require complementary paratopes for their operational recognition. An epitope that is conserved among different variants of a protein means that the same paratope can specifically recognize these different variants by contacting the same parts of the molecules.

The antibodies of the invention may be monoclonal, for example, human monoclonal antibodies, or recombinant antibodies. The invention also provides fragments of the antibodies of the invention, particularly fragments that retain the antigen-binding activity of the antibodies. Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies.

In one embodiment, the antibodies and antibody fragments of the invention neutralize at least two different group 1 subtypes or at least two different group 2 subtypes of influenza A virus. Exemplary influenza A virus subtypes include, but are not limited to, H5N1 (A/Vietnam/1203/04), H1N1 (A/New Caledonia/20/99), H1N1 (A/Salomon Island/3/2006), H3N2 (A/Wyoming/3/03) and H9N2 (A/chicken/Hong Kong/G9/97). In another embodiment, the antibodies are specific for 2, 3, 4, 5, 6, 7 or more group 1 influenza A virus subtypes or group 2 influenza A virus subtypes.

In an exemplary embodiment, the invention comprises an antibody, or an antibody fragment thereof, that is specific for influenza A virus subtypes H1 and H5 (e.g. H1N1 and H5N1). In another embodiment, the antibody or an antibody fragment thereof is specific for influenza A virus subtypes H1 and H9 (e.g. H1N1 and H9N2). In another embodiment, the antibody or antibody fragments thereof is specific for influenza A virus subtypes H1, H5 and H9 (e.g. H1N1, H5N1 and H9N2). Other exemplary subtypes of influenza A virus are provided earlier in the application.

The SEQ ID numbers for the amino acid sequence for the heavy chain variable region (VH) and the light chain variable region (VL) of exemplary antibodies of the invention are listed in Table 1.

TABLE 1

SEQ ID Numbers for VH and VL Polypeptides for Exemplary Influenza A Virus Neutralizing Antibodies

| Antibody | SEQ ID NOs for Heavy Chains | SEQ ID NOs for Light Chains |
|---|---|---|
| FB54 | 13 | 14 |
| FB139 | 29 | 30 |
| FC6 | 45 | 46 |
| FC41 | 60 | 61 |
| FE43 | 74 | 75 |
| FE53 | 89 | 90 |
| FE17 | 105 | 106 |
| FB75 | 121 | 122 |
| FB110 | 121 | 122 |
| FB177 | 121 | 122 |
| FB79 | 131 | |
| FC1c | 139 | |

In one embodiment, an antibody or antibody fragment of the invention comprises a heavy chain variable region having an amino acid sequence that is about 70%, 75%, 80%, 85%, 90%, 95%, 97%, 98%, 99% or 100% identical to the sequence recited in any one of SEQ ID NOs: 13, 29, 45, 60, 74, 89, 105, 121, 131 or 139. In another embodiment, an antibody or antibody fragment of the invention comprises a light chain variable region having an amino acid sequence that is about 70%, 75%, 80%, 85%, 90%, 95%, 97%, 98%, 99% or 100% identical to the sequence recited in any one of SEQ ID NOs: 14, 30, 46, 61, 75, 90, 106, or 122.

In yet another embodiment, the heavy chain variable region of an antibody of the invention may be encoded by a nucleic acid that has a sequence that is about 70%, 75%, 80%, 85%, 90%, 95%, 97%, 98%, 99% or 100% identical to the sequence recited in any one of SEQ ID NOs: 15, 31, 47, 62, 76, 91, 107, 123, 132 or 140. In yet another embodiment, the light chain variable region of an antibody of the invention may be encoded by a nucleic acid that has a sequence that is about 70%, 75%, 80%, 85%, 90%, 95%, 97%, 98%, 99% or 100% identical to the sequence recited in any one of SEQ ID NOs: 16, 32, 48, 63, 77, 92, 108, or 124.

The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The positions of the CDR amino acids are defined according to the IMGT numbering system as: CDR1—IMGT positions 27 to 38, CDR2—IMGT positions 56 to 65 and CDR3—IMGT positions 105 to 117.

Table 2 provides the SEQ ID NOs for the amino acid sequences of the six CDRs of the heavy and light chains, respectively, of the exemplary antibodies of the invention.

TABLE 2

SEQ ID Numbers for CDR Polypeptides of Exemplary Influenza A Virus Neutralizing Antibodies

| Antibody | SEQ ID NOs. for CDRH1, CDRH2, CDRH3 | SEQ ID NOs. for CDRL1, CDRL2, CDRL3 |
|---|---|---|
| FB54 | 1, 2, 3 | 4, 5, 6 |
| FB139 | 17, 18, 19 | 20, 21, 22 |
| FC6 | 33, 34, 35 | 36, 37, 38 |
| FC41 | 49, 50, 51 | 52, 5, 53 |
| FE43 | 64, 65, 66 | 36, 67, 68 |
| FE53 | 78, 79, 80 | 81, 21, 82 |
| FE17 | 93, 94, 95 | 96, 97, 98 |
| FB75 | 109, 110, 111 | 112, 113, 114 |
| FB110 | 109, 110, 111 | 112, 113, 114 |
| FB177 | 109, 110, 111 | 112, 113, 114 |
| FB79 | 125, 126, 127 | |
| FC1c | 133, 134, 135 | |

In one embodiment, an antibody or antibody fragment of the invention comprises at least one CDR with a sequence that has at least 95% sequence identity to any one of SEQ ID NOs: 1-6 17-22, 33-38, 49-53, 64-68, 78-82, 93-98, 109-114, 125-127, or 133-135, wherein, wherein the antibody neutralizes influenza A virus.

In another embodiment, the invention provides an antibody comprising a heavy chain comprising one or more (i.e. one, two or all three) heavy chain CDRs from FB54, FB139, FC6, FC41, FE43, FE53, FE17, FB75, FB110, FB177, FB79, FC1c, FB118, FB179, FB186, FE9b, FE25, FE54, FG20, FB15b or FC54. In an exemplary embodiment, the antibody or antigen binding fragment of the invention comprises a heavy chain CDR1 selected from the group consisting of SEQ ID NO: 1, SEQ ID NO: 17, SEQ ID NO: 33, SEQ ID NO: 49, SEQ ID NO: 64, SEQ ID NO: 78, SEQ ID NO: 93, SEQ ID NO: 109, SEQ ID NO: 125 and SEQ ID NO: 133; a heavy chain CDR2 selected from the group consisting of SEQ ID NO: 2, SEQ ID NO: 18, SEQ ID NO: 34, SEQ ID NO: 50, SEQ ID NO: 65, SEQ ID NO: 79, SEQ ID NO: 94, SEQ ID NO: 110, SEQ ID NO: 126 and SEQ ID NO: 134; and a heavy chain CDR3 selected from the group consisting of SEQ ID NO: 3, SEQ ID NO: 19, SEQ ID NO: 35, SEQ ID NO: 51, SEQ ID NO: 66, SEQ ID NO: 80, SEQ ID NO: 95, SEQ ID NO: 111, SEQ ID NO: 127 and SEQ ID NO: 135.

In yet another embodiment, the invention provides an antibody comprising a light chain comprising one or more (i.e. one, two or all three) light chain CDRs from FB54, FB139, FC6, FC41, FE43, FE53, FE17, FB75, FB110, FB177, FB79, FC1c, FB118, FB179, FB186, FE9B, FE25, FE54, FG20, FB15b or FC54. In an exemplary embodiment, the antibody or antigen binding fragment of the invention comprises a light chain CDR1 selected from the group consisting of SEQ ID NO: 4, SEQ ID NO: 20, SEQ ID NO: 36, SEQ ID NO: 52, SEQ ID NO: 81, SEQ ID NO: 96, and SEQ ID NO: 112; a light chain CDR2 selected from the group consisting of SEQ ID NO: 5, SEQ ID NO: 21, SEQ ID NO: 37, SEQ ID NO: 67, SEQ ID NO: 97, and SEQ ID NO: 113; and a light chain CDR3 selected from the group consisting of SEQ ID NO: 6, SEQ ID NO: 22, SEQ ID NO: 38, SEQ ID NO: 53, SEQ ID NO: 68, SEQ ID NO: 82, SEQ ID NO: 98, and SEQ ID NO: 114.

In an exemplary embodiment, an antibody as provided herein comprises a heavy chain comprising the amino acid sequence of SEQ ID NO: 1 for CDRH1, SEQ ID NO: 2 for CDRH2, and SEQ ID NO: 3 for CDRH3; or SEQ ID NO: 17 for CDRH1, SEQ ID NO: 18 for CDRH2, and SEQ ID NO: 19 for CDRH3; or SEQ ID NO: 33 for CDRH1, SEQ ID NO: 34 for CDRH2, and SEQ ID NO: 35 for CDRH3; or SEQ ID NO:

49 for CDRH1, SEQ ID NO: 50 for CDRH2, and SEQ ID NO: 51 for CDRH3; or SEQ ID NO: 64 for CDRH1, SEQ ID NO: 65 for CDRH2, and SEQ ID NO: 66 for CDRH3; or SEQ ID NO: 78 for CDRH1, SEQ ID NO: 79 for CDRH2, and SEQ ID NO: 80 for CDRH3; or SEQ ID NO: 93 for CDRH1, SEQ ID NO: 94 for CDRH2, and SEQ ID NO: 95 for CDRH3; or SEQ ID NO: 109 for CDRH1, SEQ ID NO:110 for CDRH2, and SEQ ID NO: 111 for CDRH3; or SEQ ID NO: 125 for CDRH1, SEQ ID NO:126 for CDRH2, and SEQ ID NO: 127 for CDRH3; or SEQ ID NO: 133 for CDRH1, SEQ ID NO: 134 for CDRH2, and SEQ ID NO: 135 for CDRH3.

In an exemplary embodiment, an antibody as provided herein comprises a light chain comprising the amino acid sequence of SEQ ID NO: 4 for CDRL1, SEQ ID NO: 5 for CDRL2, and SEQ ID NO: 6 for CDRL3; or SEQ ID NO: 20 for CDRL1, SEQ ID NO; 21 for CDRL2, and SEQ ID NO: 22 for CDRL3; or SEQ ID NO: 36 for CDRL1, SEQ ID NO: 37 for CDRL2, and SEQ ID NO: 38 for CDRL3; or SEQ ID NO: 52 for CDRL1, SEQ ID NO: 5 for CDRL2, and SEQ ID NO: 53 for CDRL3; or SEQ ID NO: 36 for CDRL1, SEQ ID NO: 67 for CDRL2, and SEQ ID NO: 68 for CDRL3; or SEQ ID NO: 81 for CDRL1, SEQ ID NO: 21 for CDRL2, and SEQ ID NO: 82 for CDRL3; or SEQ ID NO: 96 for CDRL1, SEQ ID NO: 97 for CDRL2, and SEQ ID NO: 98 for CDRL3; or SEQ ID NO: 112 for CDRL1, SEQ ID NO:113 for CDRL2, and SEQ ID NO: 114 for CDRL3.

In one embodiment, an antibody of the invention, or antigen binding fragment thereof, comprises all of the CDRs of antibody FB54 as listed in Table 2, and neutralizes influenza A virus infection. In another embodiment, an antibody of the invention, or antigen binding fragment thereof, comprises all of the CDRs of antibody FB139 as listed in Table 2, and neutralizes influenza A virus infection. In yet another embodiment, an antibody of the invention, or antigen binding fragment thereof, comprises all of the CDRs of antibody FC6 as listed in Table 2, and neutralizes influenza A virus infection. In still another embodiment, an antibody of the invention, or antigen binding fragment thereof, comprises all of the CDRs of antibody FC41 as listed in Table 2, and neutralizes influenza A virus infection. In yet another embodiment, an antibody of the invention, or antigen binding fragment thereof, comprises all of the CDRs of antibody FE43 as listed in Table 2, and neutralizes influenza A virus infection. In yet another embodiment, an antibody of the invention, or antigen binding fragment thereof, comprises all of the CDRs of antibody FE53 as listed in Table 2, and neutralizes influenza A virus infection.

In yet another embodiment, an antibody of the invention, or antigen binding fragment thereof, comprises all of the CDRs of antibody FE17 as listed in Table 2, and neutralizes influenza A virus infection. In yet another embodiment, an antibody of the invention, or antigen binding fragment thereof, comprises all of the CDRs of antibody FB75 as listed in Table 2, and neutralizes influenza A virus infection. In yet another embodiment, an antibody of the invention, or antigen binding fragment thereof, comprises all of the CDRs of antibody FB110 as listed in Table 2, and neutralizes influenza A virus infection. In yet another embodiment, an antibody of the invention, or antigen binding fragment thereof, comprises all of the CDRs of antibody FB177 as listed in Table 2, and neutralizes influenza A virus infection. In yet another embodiment, an antibody of the invention, or antigen binding fragment thereof, comprises all of the CDRs of antibody FB79 as listed in Table 2, and neutralizes influenza A virus infection. In yet another embodiment, an antibody of the invention, or antigen binding fragment thereof, comprises all of the CDRs of antibody FC1 c as listed in Table 2, and neutralizes influenza A virus infection.

Exemplary antibodies of the invention include, but are not limited to, FB54, FB139, FC6, FC41, FE43, FE53, FE17, FB75, FB 110, FB177, FB79, FC1c, FB 118, FB179, FB186, FE9b, FE25, FE54, FG20, FB15b or FC54.

The invention further comprises an antibody, or fragment thereof, that binds to the same epitope as an antibody of the invention, or an antibody that competes with an antibody of the invention.

Antibodies of the invention also include hybrid antibody molecules that comprise one or more CDRs from an antibody of the invention and one or more CDRs from another antibody to the same epitope. In one embodiment, such hybrid antibodies comprise three CDRs from an antibody of the invention and three CDRs from another antibody to the same epitope. Exemplary hybrid antibodies comprise i) the three light chain CDRs from an antibody of the invention and the three heavy chain CDRs from another antibody to the same epitope, or ii) the three heavy chain CDRs from an antibody of the invention and the three light chain CDRs from another antibody to the same epitope.

Variant antibodies are also included within the scope of the invention. Thus, variants of the sequences recited in the application are also included within the scope of the invention. Such variants include natural variants generated by somatic mutation in vivo during the immune response or in vitro upon culture of immortalized B cell clones. Alternatively, variants may arise due to the degeneracy of the genetic code, as mentioned above or may be produced due to errors in transcription or translation.

Further variants of the antibody sequences having improved affinity and/or potency may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

In one embodiment variant antibody sequences may share 70% or more (i.e. 75%, 80%, 85%, 90%, 95%, 97%, 98%, 99% or more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

In another aspect, the invention also includes nucleic acid sequences encoding part or all of the light and heavy chains and CDRs of the antibodies of the present invention. Provided herein are nucleic acid sequences encoding part or all of the light and heavy chains and CDRs of exemplary antibodies of the invention. Table 3 provides the SEQ ID numbers for the nucleic acid sequences encoding the CDRs, heavy chain and light chain variable regions of the exemplary antibodies of the invention. Due to the redundancy of the genetic code, variants of these sequences will exist that encode the same amino acid sequences.

TABLE 3

SEQ ID Numbers for CDRs, VH and VL Polynucleotides of Exemplary Influenza A Virus Neutralizing Antibodies

| Antibody | SEQ ID NO for Nucleic Acids encoding CDRs (CDRH1, CDRH2, CDRH3, CDRL1, CDRL2, CDRL3) | SEQ ID NO for Heavy Chain Nucleic Acid Sequences | SEQ ID NO for Light Chain Nucleic Acid Sequences |
|---|---|---|---|
| FB54 | 7-12 | 15 | 16 |
| FB139 | 23-28 | 31 | 32 |
| FC6 | 39-44 | 47 | 48 |
| FC41 | 54-59 | 62 | 63 |
| FE43 | 69-71, 42, 72, 73 | 76 | 77 |
| FE53 | 83-88 | 91 | 92 |
| FE17 | 99-104 | 107 | 108 |
| FB75 | 115-120 | 123 | 124 |
| FB110 | 115-120 | 123 | 124 |
| FB177 | 115-120 | 123 | 124 |
| FB79 | 128-130 | 132 | |
| FC1c | 136-138 | 140 | |

In one embodiment variant antibody sequences may share 70% or more (i.e. 75%, 80%, 85%, 90%, 95%, 97%, 98%, 99% or more) amino acid sequence identity with the sequences recited in the application. In another embodiment, a nucleic acid sequence of the invention has the sequence of a nucleic acid encoding a heavy or light chain CDR of an antibody of the invention. For example, a nucleic acid sequence according to the invention comprises a sequence that is at least 75% identical to the nucleic acid sequences of SEQ ID NOs: 7-12, 15, 16, 23-28, 31, 32, 39-44, 47, 48, 54-59, 62, 63, 69-73, 76, 77, 83-88, 91, 92, 99-104, 107, 108, 115-120, 123, 124, 128-130, 132, 136-138, or 140.

Further included within the scope of the invention are vectors, for example expression vectors, comprising a nucleic acid sequence according to the invention. Cells transformed with such vectors are also included within the scope of the invention. Examples of such cells include but are not limited to, eukaryotic cells, e.g. yeast cells, animal cells or plant cells. In one embodiment the cells are mammalian, e.g. human, CHO, HEK293T, PER.C6, NS0, myeloma or hybridoma cells.

The invention also relates to monoclonal antibodies that bind to an epitope capable of binding the antibodies of the invention, including, but not limited to, a monoclonal antibody selected from the group consisting of FB54, FB139, FC6, FC41, FE43, FE53, FE17, FB75, FB110, FB177, FB79, FC1c, FB118, FB179, FB186, FE9b, FE25, FE54, FG20, FB15b and FC54.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme. The antibodies may also be used for the molecular identification and characterization (epitope mapping) of antigens.

Antibodies of the invention can be coupled to a drug for delivery to a treatment site or coupled to a detectable label to facilitate imaging of a site comprising cells of interest, such as cells infected with influenza A virus. Methods for coupling antibodies to drugs and detectable labels are well known in the art, as are methods for imaging using detectable labels.

Labelled antibodies may be employed in a wide variety of assays, employing a wide variety of labels.

Detection of the formation of an antibody-antigen complex between an antibody of the invention and an epitope of interest (an influenza A virus epitope) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}I$, $^{131}I$, $^{35}S$, or $^{3}H$. Such labelled reagents may be used in a variety of well-known assays, such as radioimmunoassays, enzyme immunoassays, e.g., ELISA, fluorescent immunoassays, and the like. (See U.S. Pat. Nos. 3,766,162; 3,791,932; 3,817,837; and 4,233,402 for example).

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Amon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-256; ed. Hellstrom et al. (1987) "Antibodies for Drug Delivery," in *Controlled Drug Delivery*, ed. Robinson et al. (2d ed; Marcel Dekker, Inc.), pp. 623-653; Thorpe (1985) "Antibody Carriers of Cytotoxic Agents in Cancer Therapy: A Review," in *Monoclonal Antibodies '84: Biological and Clinical Applications*, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in *Monoclonal Antibodies for Cancer Detection and Therapy*, ed. Baldwin et al. (Academic Press, New York, 1985), pp. 303-316; and Thorpe et al. (1982) *Immunol. Rev.* 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention (e.g. U.S. Pat. No. 4,831,175). Antibodies or, antigen-binding fragments thereof may be directly labelled with radioactive iodine, indium, yttrium, or other radioactive particle known in the art (e.g. U.S. Pat. No. 5,595,721). Treatment may consist of a combination of treatment with conjugated and non-conjugated antibodies administered simultaneously or subsequently (e.g. WO00/52031; WO00/52473).

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. Nos. 4,766,106; 4,179,337; 4,495,285 and 4,609,546. In some embodiments the polymers may be selected from polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. In one embodiment the protective group may have between 1 and 8 carbons. In a further embodiment the protective group is methyl. The symbol n is a positive integer. In one embodiment n is between 1 and 1,000. In another embodiment n is between 2 and 500. In one embodiment the PEG has an average molecular weight between 1,000 and 40,000. In a further embodiment the PEG has a molecular weight between 2,000 and 20,000. In yet a further embodiment the PEG has a molecular weight between 3,000 and 12,000. In one embodiment PEG has at least one hydroxy group. In another embodiment the PEG has a terminal hydroxy group. In yet another embodiment it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. In some embodiments POG has a molecular weight in the same range as PEG. Another drug delivery system that can be used for increasing circulatory half-life is the liposome. Methods of preparing liposome delivery systems are discussed in Gabizon et al. (1982), Cafiso (1981) and Szoka (1980). Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention may be immunogenic in non-human (or heterologous) hosts e.g. in mice. In particular, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

Antibodies of the invention can be of any isotype (e.g. IgA, IgG, IgM i.e. an α, γ or μ heavy chain), but will generally be IgG. Within the IgG isotype, antibodies may be IgG1, IgG2, IgG3 or IgG4 subclass. Antibodies of the invention may have a κ or a λ light chain.

Production of Antibodies

Antibodies according to the invention can be made by any method known in the art. For example, the general methodology for making monoclonal antibodies using hybridoma technology is well known (Kohler, G. and Milstein, C,. 1975; Kozbar et al. 1983). In one embodiment, the alternative EBV immortalization method described in WO2004/076677 is used.

Using the method described in reference WO2004/076677, B cells producing the antibody of the invention can be transformed with EBV in the presence of a polyclonal B cell activator. Transformation with EBV is a standard technique and can easily be adapted to include polyclonal B cell activators.

Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Using the method described in UK Patent Application 0819376.5, single plasma cells can be cultured in microwell culture plates. Antibodies can be isolated from the single plasma cell cultures. Further, from single plasma cell cultures, RNA can be extracted and single cell PCR can be performed using methods known in the art. The VH and VL regions of the antibodies can be amplified by RT-PCR, sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" may include Fab, Fab', $F(ab')_2$ and Fv fragments. The invention also encompasses single-chain Fv fragments (scFv) derived from the heavy and light chains of an antibody of the invention e.g. the invention includes a scFv comprising the CDRs from an antibody of the invention. Also included are heavy or light chain monomers and dimers, single domain heavy chain antibodies, single domain light chain antibodies, as well as single chain antibodies, e.g. single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, Nature Biotechnology 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a host cell, and ii) isolating the expressed antibody product. Additionally, the method may include iii) purifying the antibody.

Screening of Transformed B Cells, Cultured Single Plasma Cells and Transfected HEK293T Cells Transformed B cells and cultured single plasma cells may be screened for those producing antibodies of the desired specificity or function.

The screening step may be carried out by any immunoassay, for example, ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g. to select neutralizing antibodies rather than just antigen-binding antibodies, to select antibodies that can change characteristics of targeted cells, such as their signalling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured single plasma cells can be isolated, cloned and expressed in HEK293T cells or other host cells using methods known in the art.

The immortalized B cell clones or the transfected HEK293T cells of the invention can be used in various ways e.g. as a source of monoclonal antibodies, as a source of nucleic acid (DNA or mRNA) encoding a monoclonal antibody of interest, for research, etc.

The invention provides a composition comprising immortalized B memory cells or transfected host cells that produce antibodies that neutralize at least two different group 1 subtypes or at least two different group 2 subtypes of influenza A virus.

Epitopes

As mentioned above, the antibodies of the invention can be used to map the epitopes to which they bind. The inventors have discovered that the antibodies neutralizing influenza A virus infection are directed towards epitopes found on HA. In one embodiment, the antibodies are directed to one or more epitopes in the stem region or in the globular head region of HA that are conserved among two or more influenza A virus subtypes. The epitopes to which the antibodies of the invention bind may be linear (continuous) or conformational (discontinuous).

The epitopes recognized by the antibodies of the present invention may have a number of uses. The epitope and mimotopes thereof in purified or synthetic form can be used to raise immune responses (i.e. as a vaccine, or for the production of antibodies for other uses) or for screening sera for antibodies that immunoreact with the epitope or mimotopes thereof. In one embodiment such an epitope or mimotope, or antigen comprising such an epitope or mimotope may be used as a vaccine for raising an immune response. The antibodies and antibody fragments of the invention can also be used in a method of monitoring the quality of vaccines. In particular the antibodies can be used to check that the antigen in a vaccine contains the correct immunogenic epitope in the correct conformation.

The epitope may also be useful in screening for ligands that bind to said epitope. Such ligands, include but are not limited to antibodies; including those from camels, sharks and other species, fragments of antibodies, peptides, phage display technology products, aptamers, adnectins or fragments of other viral or cellular proteins, may block the epitope and so prevent infection. Such ligands are encompassed within the scope of the invention.

Recombinant Expression

The immortalized B cell clone or the cultured plasma cell of the invention may also be used as a source of nucleic acid for the cloning of antibody genes for subsequent recombinant expression. Expression from recombinant sources is more common for pharmaceutical purposes than expression from B cells or hybridomas e.g. for reasons of stability, reproducibility, culture ease, etc.

Thus the invention provides a method for preparing a recombinant cell, comprising the steps of: (i) obtaining one or more nucleic acids (e.g. heavy and/or light chain mRNAs) from the B cell clone or the cultured single plasma cell that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured single plasma cell that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

The invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured single plasma cell of the invention. Thus the procedures for first preparing the nucleic acid(s) and then using it to transfect a host cell can be performed at different times by different people in different places (e.g. in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells or plasma cells are well known in the art (e.g. see Chapter 4 of *Kuby Immunology*, 4th edition, 2000).

The transfected host cell may be a eukaryotic cell, including yeast and animal cells, particularly mammalian cells (e.g. CHO cells, NS0 cells, human cells such as PER.C6 (Jones et al 2003) or HKB-11 (Cho et al. 2001; Cho et al. 2003) cells, myeloma cells (U.S. Pat. Nos. 5,807,715; 6,300,104 etc.)), as well as plant cells. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention provides a method for preparing one or more nucleic acid molecules (e.g.

heavy and light chain genes) that encode an antibody of interest, comprising the steps of: (i) preparing an immortalized B cell clone or culturing a plasma cell according to the invention; (ii) obtaining from the B cell clone or the cultured single plasma cell nucleic acid that encodes the antibody of interest. The invention also provides a method for obtaining a nucleic acid sequence that encodes an antibody of interest, comprising the steps of: (i) preparing an immortalized B cell clone or culturing a single plasma cell according to the invention; (ii) sequencing nucleic acid from the B cell clone or the cultured plasma cell that encodes the antibody of interest.

The invention also provides a method of preparing nucleic acid molecule(s) that encodes an antibody of interest, comprising the step of obtaining the nucleic acid that was obtained from a transformed B cell clone or a cultured plasma cell of the invention. Thus the procedures for first obtaining the B cell clone or the cultured plasma cell, and then obtaining nucleic acid(s) from the B cell clone or the cultured plasma cell can be performed at different times by different people in different places (e.g. in different countries).

The invention provides a method for preparing an antibody (e.g. for pharmaceutical use), comprising the steps of: (i) obtaining and/or sequencing one or more nucleic acids (e.g. heavy and light chain genes) from the selected B cell clone or the cultured plasma cell expressing the antibody of interest; (ii) inserting the nucleic acid(s) into or using the nucleic acid(s) sequence(s) to prepare an expression vector; (iii) transfect a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of: culturing or sub-culturing a transfected host cell population under conditions where the antibody of interest is expressed and, optionally, purifying the antibody of interest, wherein said transfected host cell population has been prepared by (i) providing nucleic acid(s) encoding a selected antibody of interest that is produced by a B cell clone or a cultured plasma cell prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest. Thus the procedures for first preparing the recombinant host cell and then culturing it to express antibody can be performed at very different times by different people in different places (e.g. in different countries).

Pharmaceutical Compositions

The invention provides a pharmaceutical composition containing the antibodies and/or antibody fragments of the invention and/or nucleic acid encoding such antibodies and/or the epitopes recognized by the antibodies of the invention. A pharmaceutical composition may also contain a pharmaceutically acceptable carrier to allow administration. The carrier should not itself induce the production of antibodies harmful to the individual receiving the composition and should not be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Within the scope of the invention, forms of administration may include those forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid.

Once formulated, the compositions of the invention can be administered directly to the subject. In one embodiment the compositions are adapted for administration to human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g. whether a pharmaceutical should be delivered daily, weekly, monthly, etc. Frequency and dosage may also depend on the severity of symptoms.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition, like Synagis™ and Herceptin™, for reconstitution with sterile water containing a preservative). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a subject. For example, a lyophilised antibody can be provided in kit form with sterile water or a sterile buffer.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in further embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Pharmaceutical compositions will include an effective amount of one or more antibodies of the invention and/or a polypeptide comprising an epitope that binds an antibody of the invention i.e. an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g. Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc.

In one embodiment the compositions can include more than one (e.g. 2, 3, 4, 5, etc.) antibodies of the invention to provide an additive or synergistic therapeutic effect. In another embodiment, the composition may comprise one or more (e.g. 2, 3, 4, 5, etc.) antibodies of the invention and one or more (e.g. 2, 3, 4, 5, etc.) additional antibodies against influenza A virus. For example, one antibody may bind to a HA epitope, while another may bind to a different epitope on HA (e.g., one may bind to an epitope in the stem region while another may bind to an epitope in the globular head region), or to an epitope on the neuraminidase and/or matrix proteins. Further, the administration of antibodies of the invention together with an influenza A vaccine or with antibodies of specificities other than influenza A virus are within the scope of the invention. The antibodies of the invention can be administered either combined/simultaneously or at separate times from an influenza A vaccine or from antibodies of specificities other than influenza A virus.

In another embodiment, the invention provides a pharmaceutical composition comprising two or more antibodies, wherein the first antibody is an antibody of the invention and is specific for a HA epitope, and the second antibody is specific for a neuraminidase epitope, a second HA epitope and/or a matrix epitope. For example, the invention provides a pharmaceutical composition comprising two or more antibodies, wherein the first antibody is an antibody of the invention and is specific for an epitope in the stem of an influenza A virus HA, and the second antibody is specific for a neuraminidase epitope, an epitope in the globular head of HA, a second epitope in the stem of HA and/or a matrix epitope. The second epitope in the stem or the epitope in the globular head of the influenza A virus HA may, but need not, be conserved among more than one influenza A virus subtype.

In another example, the invention provides a pharmaceutical composition comprising two or more antibodies, wherein the first antibody is an antibody of the invention and is specific for an epitope in the globular head of an influenza A virus HA, and the second antibody is specific for a neuraminidase epitope, an epitope in the stem of HA, a second epitope in the globular head of HA and/or a matrix epitope. The second epitope in the globular head or the epitope in the stem of the influenza A virus HA may, but need not, be conserved among more than one influenza A virus subtype.

In yet another embodiment, the invention provides a pharmaceutical composition comprising two or more antibodies, wherein the first antibody is specific for a neuraminidase epitope, and the second antibody is specific for a second neuraminidase epitope, a HA epitope and/or a matrix epitope.

In still another embodiment, the invention provides a pharmaceutical composition comprising two or more antibodies, wherein the first antibody is specific for a matrix epitope, and the second antibody is specific for a second matrix epitope, an epitope on HA and/or neuraminidase.

In one embodiment, antibodies of the invention specific for an influenza A virus target protein include, but are not limited to, FB54, FB139, FC6, FC41, FE43, FE53, FE17, FB75, FB110, FB177, FB79, FC1c, FB118, FB179, FB186, FE9b, FE25, FE54, FG20, FB15b or FC54. In another embodiment, antibodies of the invention specific for an influenza A virus target protein include, but are not limited to, FB54, FB139, FC6, FC41, FE43, FE53, FE17, FB75, FB110, FB177, FB79 or FC1c.

In one embodiment, the invention provides a pharmaceutical composition comprising the antibody FB54, or an antigen binding fragment thereof, and a pharmaceutically acceptable carrier. In another embodiment, the invention provides a pharmaceutical composition comprising the antibody FB139, or an antigen binding fragment thereof, and a pharmaceutically acceptable carrier. In yet another embodiment, the invention provides a pharmaceutical composition comprising the antibody FC6, or an antigen binding fragment thereof, and a pharmaceutically acceptable carrier. In still another embodiment, the invention provides a pharmaceutical composition comprising the antibody FC41, or an antigen binding fragment thereof, and a pharmaceutically acceptable carrier. In yet another embodiment, the invention provides a pharmaceutical composition comprising the antibody FE43, or an antigen binding fragment thereof, and a pharmaceutically acceptable carrier. In yet another embodiment, the invention provides a pharmaceutical composition comprising the antibody FE53, or an antigen binding fragment thereof, and a pharmaceutically acceptable carrier.

In yet another embodiment, the invention provides a pharmaceutical composition comprising the antibody FE17, or an antigen binding fragment thereof, and a pharmaceutically acceptable carrier. In yet another embodiment, the invention provides a pharmaceutical composition comprising the antibody FB75, or an antigen binding fragment thereof, and a pharmaceutically acceptable carrier. In yet another embodiment, the invention provides a pharmaceutical composition comprising the antibody FB110, or an antigen binding fragment thereof, and a pharmaceutically acceptable carrier. In yet another embodiment, the invention provides a pharmaceutical composition comprising the antibody FB177, or an antigen binding fragment thereof, and a pharmaceutically acceptable carrier. In yet another embodiment, the invention provides a pharmaceutical composition comprising the antibody FB79, or an antigen binding fragment thereof, and a pharmaceutically acceptable carrier. In yet another embodiment, the invention provides a pharmaceutical composition comprising the antibody FC1c, or an antigen binding fragment thereof, and a pharmaceutically acceptable carrier.

Antibodies of the invention may be administered (either combined or separately) with other therapeutics e.g. with chemotherapeutic compounds, with radiotherapy, etc. In one embodiment, the therapeutic compounds include anti-viral compounds such as Tamiflu™. Such combination therapy provides an additive or synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Antibodies may be administered to those subjects who have previously shown no response to treatment for influenza A virus infection, i.e. have been shown to be refractive to anti-influenza A treatment. Such treatment may include previous treatment with an anti-viral agent. This may be due to, for example, infection with an anti-viral resistant strain of influenza A virus.

In one embodiment, a composition of the invention may include antibodies of the invention, wherein the antibodies may make up at least 50% by weight (e.g. 60%, 70%, 75%, 80%, 85%, 90%, 95%, 97%, 98%, 99% or more) of the total protein in the composition. In such a composition, the antibodies are in purified form.

The invention provides a method of preparing a pharmaceutical, comprising the steps of: (i) preparing an antibody of the invention; and (ii) admixing the purified antibody with one or more pharmaceutically-acceptable carriers.

The invention also provides a method of preparing a pharmaceutical, comprising the step of admixing an antibody with one or more pharmaceutically-acceptable carriers, wherein the antibody is a monoclonal antibody that was obtained from a transformed B cell or a cultured plasma cell of the invention. Thus the procedures for first obtaining the monoclonal antibody and then preparing the pharmaceutical can be performed at very different times by different people in different places (e.g. in different countries).

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cell to a subject, such that the nucleic acid can be expressed in the subject in situ to provide a desired therapeutic effect. Suitable gene therapy and nucleic acid delivery vectors are known in the art.

Compositions of the invention may be immunogenic compositions, and in some embodiments may be vaccine compositions comprising an antigen comprising an epitope recognized by an antibody of the invention. Vaccines according to the invention may either be prophylactic (i.e. to prevent infection) or therapeutic (i.e. to treat infection).

Compositions may include an antimicrobial, particularly if packaged in a multiple dose format. They may comprise detergent e.g. a Tween (polysorbate), such as Tween 80. Detergents are generally present at low levels e.g. <0.01%. Compositions may also include sodium salts (e.g. sodium chloride) to give tonicity. A concentration of 10±2 mg/ml NaCl is typical.

Further, compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

The compositions of the invention may also comprise one or more immunoregulatory agents. In one embodiment, one or more of the immunoregulatory agents include(s) an adjuvant.

The epitope compositions of the invention may elicit both a cell mediated immune response as well as a humoral immune response in order to effectively address influenza A virus infection. This immune response may induce long lasting (e.g. neutralizing) antibodies and a cell mediated immunity that can quickly respond upon exposure to influenza A virus.

Medical Treatments and Uses

The antibodies and antibody fragments of the invention or derivatives and variants thereof may be used for the treatment of influenza A virus infection, for the prevention of influenza A virus infection or for the diagnosis of influenza A virus infection.

Methods of diagnosis may include contacting an antibody or an antibody fragment with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of diagnosis may also include the detection of an antigen/antibody complex.

The invention therefore provides (i) an antibody, an antibody fragment, or variants and derivatives thereof according to the invention, (ii) an immortalized B cell clone according to the invention, (iii) an epitope capable of binding an antibody of the invention or (iv) a ligand, preferably an antibody, capable of binding an epitope that binds an antibody of the invention for use in therapy.

The invention also provides a method of treating a subject comprising administering to the subject an antibody, an antibody fragment, or variants and derivatives thereof according to the invention, or a ligand, preferably an antibody, capable of binding an epitope that binds an antibody of the invention. In one embodiment, the method results in reduced influenza A virus infection in the subject. In another embodiment, the method prevents, reduces the risk or delays influenza A virus infection in the subject.

The invention also provides the use of (i) an antibody, an antibody fragment, or variants and derivatives thereof according to the invention, (ii) an immortalized B cell clone according to the invention, (iii) an epitope capable of binding an antibody of the invention, or (iv) a ligand, preferably an antibody, that binds to an epitope capable of binding an antibody of the invention, in the manufacture of a medicament for the prevention or treatment of influenza A virus infection.

The invention provides a composition of the invention for use as a medicament for the prevention or treatment of a influenza A virus infection. It also provides the use of an antibody of the invention and/or a protein comprising an epitope to which such an antibody binds in the manufacture of a medicament for treatment of a subject and/or diagnosis in a subject. It also provides a method for treating a subject, comprising the step of administering to the subject a composition of the invention. In some embodiments the subject may be a human. One way of checking efficacy of therapeutic treatment involves monitoring disease symptoms after administration of the composition of the invention. Treatment can be a single dose schedule or a multiple dose schedule.

In one embodiment, an antibody, antibody fragment, immortalized B cell clone, epitope or composition according to the invention is administered to a subject in need of such treatment. Such a subject includes, but is not limited to, one who is particularly at risk of or susceptible to influenza A virus infection, including, for example, an immunocompromised subject.

The antibody or antibody fragment of the invention can be used in passive immunization or active vaccination.

Antibodies and fragments thereof as described in the present invention may also be used in a kit for the diagnosis of influenza A virus infection. Further, epitopes capable of binding an antibody of the invention may be used in a kit for monitoring the efficacy of vaccination procedures by detecting the presence of protective anti-influenza A virus antibodies. Antibodies, antibody fragment, or variants and derivatives thereof, as described in the present invention may also be used in a kit for monitoring vaccine manufacture with the desired immunogenicity.

The invention also provides a method of preparing a pharmaceutical, comprising the step of admixing a monoclonal antibody with one or more pharmaceutically-acceptable carriers, wherein the monoclonal antibody is a monoclonal antibody that was obtained from a transfected host cell of the invention. Thus the procedures for first obtaining the monoclonal antibody (e.g. expressing it and/or purifying it) and then admixing it with the pharmaceutical carrier(s) can be performed at very different times by different people in different places (e.g. in different countries).

Starting with a transformed B cell or a cultured plasma cell of the invention, various steps of culturing, sub-culturing, cloning, sub-cloning, sequencing, nucleic acid preparation etc. can be performed in order to perpetuate the antibody expressed by the transformed B cell or the cultured plasma cell, with optional optimization at each step. In a preferred embodiment, the above methods further comprise techniques of optimization (e.g. affinity maturation or optimization) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or amend certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g. 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g. labels) or can introduce tags (e.g. for purification purposes). Mutations can be introduced in specific sites or can be introduced at random, followed by selection (e.g. molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Moreover, changes achieved in independent steps may be combined. Different properties introduced into the encoded amino acids may include, but are not limited to, enhanced affinity.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1

Generation of Immortalized B Cells and Identification of Heterosubtypic Antibodies against Influenza A Virus Healthy volunteers were vaccinated with seasonal influenza vaccine. Early after vaccination (2 weeks), vaccine-specific IgG antibody titer increased in the plasma of all donors. To detect a possible heterologous antibody response, the sera were tested for their capacity to neutralize pseudotypes carrying H5 HA from A/VN/1194/04. Remarkably, several donors showed a pre-boost heterosubtypic serum neutralizing activity, which was boosted by vaccination, reaching in some individuals IC50 titers as high as 20,000 (data not shown). These results suggest that some individuals have memory B cells specific for conserved epitopes shared by H1 and H5 HAs that can be recalled by influenza vaccines.

To characterize the heterosubtypic antibody response observed at the polyclonal level, memory B cells were isolated from cryopreserved peripheral blood mononuclear cells (PBMC) collected two weeks after vaccination from four donors that mounted the strongest H5-neutralizing response upon vaccination. $CD22^+$ $IgM^-$, $IgD^-$, $IgA^-$ $IgG^+$ memory B cells were immortalized with EBV in the presence of CpG oligodeoxynucleotide 2006 and irradiated allogeneic PBMC. After two weeks the culture supernatants were screened for the presence of H5-pseudotype neutralizing antibodies. Positive cultures were further tested using binding and neutralization assays performed with an infectious H1N1 virus (A/SI/3/2006). Cultures that scored positive for both H5-pseudotype and H1N1 virus neutralization were subcloned and antibodies purified by affinity chromatography for further characterization.

From the first screening we isolated 18 monoclonal antibodies that bound to H1 and H5 HA in ELISA and showed different capacity to neutralize H5-pseudotypes (H5pp) and H5N1, H1N1, H3N2 and H9N2 infectious viruses (Table 4).

TABLE 4

| | Binding HA | | Neutralization (μg/ml) | | | | | |
|---|---|---|---|---|---|---|---|---|
| | | | H5pp(1) IC90 | H5N1(2) IC50 | H1N1(2) IC90 | | H3N2(2) IC50 | H9N2(2) IC50 A/ck/ |
| | ELISA | | A/VN/ | A/VN/ | A/NC/ | A/SI/ | A/WY/ | HK/ |
| Ab | H5 | H1 | 1194/04 | 1203/04 | 20/99 | 3/06 | 3/03 | G9/97 |
| FE17 | ++ | ++ | 0.3 | 0.7 | 0.05 | 0.2 | 16.6 | 16.6 |
| FC41 | ++ | + | 0.001 | 5 | 6.2 | 6.2 | >50 | 0.1 |
| FE43 | ++ | +/− | 0.03 | >50 | 6.2 | 6.2 | >50 | 0.02 |
| FE53 | ++ | + | 0.008 | >50 | 6.2 | 6.2 | >50 | 0.1 |
| FE54 | ++ | + | 0.04 | >50 | 6.2 | 6.2 | >50 | 0.2 |
| FB79 | ++ | + | 0.005 | >50 | 12.5 | 12.5 | >50 | 0.8 |
| FC1c | ++ | + | 0.02 | >50 | 25 | 12.5 | >50 | 0.6 |
| FB75 | ++ | + | 0.002 | >50 | 3.1 | 6.2 | >50 | 5 |
| FC36 | − | + | 14 | >50 | 3.1 | 1.6 | >50 | >50 |
| FB15b | + | + | 0.04 | >50 | 6.2 | 6.2 | >50 | >50 |
| FC54 | + | +/− | 0.4 | >50 | >50 | >50 | >50 | 0.6 |
| FA14 | + | ++ | 1.6 | >50 | nd | nd | 25 | 6.2 |
| FE89 | + | + | 0.3 | nd | 0.03 | 0.5 | nd | nd |
| FC50 | ++ | +/− | 0.02 | nd | 12.5 | 12.5 | nd | nd |
| FC6 | + | + | 0.04 | nd | 12.5 | 12.5 | nd | nd |
| FB54 | ++ | +/− | 0.001 | nd | 25 | 12.5 | nd | nd |
| FE11b | ++ | + | 0.03 | nd | 25 | 12.5 | nd | nd |
| FE9b | ++ | + | 0.01 | nd | 25 | 25 | nd | nd |
| FA6(3) | − | + | >50 | >50 | 0.05 | 0.05 | >50 | 5 |
| FC98(3) | − | ++ | >50 | >50 | 0.4 | 0.1 | >50 | 6.2 |

(1)Different antibody concentrations were incubated with H5-pseudotypes and added to HEK293T cells as described (Temperton, et al., Emerg Infect Dis 11, 411-416, 2005). Luciferase activity was measured on day 3.

(2)Different antibody concentrations were incubated with 100 $TCID_{50}$ of virus for 1 hr at room temperature prior to addition to monolayers of MDCK cells. Cell monolayers were incubated for a further 2-3 days and examined for cytopathic effect (CPE). Neutralizing titer was defined as the reciprocal of the lowest antibody concentration at which the infectivity of 100 $TCID_{50}$ of the appropriate wild-type virus for MDCK cells was completely neutralized in 50% of the wells. Infectivity was identified by the presence of CPE on day 4 and the titer was calculated by the Reed-Muench method.

(3)H1-specific antibodies (FA6 and FC98) were included as a control.

From a second screening we isolated additional 8 monoclonal antibodies. These antibodies, together with 13 antibodies isolated from the first screening, were further characterized for binding to HA from different influenza A virus subtypes (Table 5).

TABLE 5

| | ELISA (K50, μg/ml) | | | | | | |
|---|---|---|---|---|---|---|---|
| | H1 | | H5 | | | | |
| Ab | A/ Texas/ 3/99 | A/SI/ 3/06 | A/VN/ 1203/04 | A/ INDO/ 5/05 | H9 A/HK/ 1073/99 | H3 A/WY/ 3/03 | H7 A/NL/ 219/03 |
| FB54 | 0.018 | 0.186 | 0.023 | 38.707 | 2.565 | — | — |
| FB79 | 0.021 | 0.735 | 0.023 | 4.406 | 53.081 | — | — |
| FB118 | 0.105 | 0.196 | 0.058 | 0.490 | 1.401 | — | — |
| FB139 | 0.060 | 1.384 | 0.033 | 0.163 | 0.066 | — | — |
| FB179 | 0.095 | 0.667 | 1.944 | 11.805 | 0.138 | — | — |
| FB186 | 0.048 | 0.530 | 0.065 | 44.191 | — | — | — |
| FC6 | 0.066 | 1.469 | 0.157 | — | 0.150 | — | — |
| FC41 | 0.027 | 0.545 | 0.031 | 0.264 | 0.034 | — | — |
| FE9b | 0.024 | 0.841 | 0.043 | — | 8.693 | — | — |
| FE25 | 0.048 | 2.962 | 0.105 | — | 0.068 | — | — |
| FE43 | 0.013 | 0.206 | 0.029 | 4.544 | 0.307 | — | — |
| FE53 | 0.015 | 0.375 | 0.015 | 0.084 | 0.014 | — | — |
| FE54 | 0.020 | 1.939 | 0.022 | 0.089 | 0.047 | — | — |
| FG20 | 0.128 | 7.276 | 0.582 | — | — | — | — |
| FB15b | 0.046 | 1.381 | 0.928 | — | — | — | — |
| FB75 | 0.023 | 0.140 | 0.022 | 0.041 | — | — | — |
| FB110 | 0.130 | 1.592 | 0.044 | 13.715 | — | — | — |
| FB177 | 0.070 | 0.534 | 0.014 | 0.723 | — | — | — |
| FC1c | 0.014 | 0.291 | 0.010 | 0.035 | — | — | — |
| FE17 | 0.033 | 0.058 | 0.117 | — | — | — | — |
| FC54 | 1.462 | 7.142 | 0.987 | 3.877 | 1.177 | — | — |

The symbol — indicates that the antibody did not neutralize at the highest concentration tested.

The antibodies were then functionally characterized in a pseudotype neutralization assay (Table 6). Most antibodies showed a broad pattern of neutralization against all H5 pseudotypes representative of clades 0, 1, 2.1, 2.2 and 2.3. Some antibodies, such as FB54, FB110, FC6, FC41 and FE43, were very potent as they neutralized pseudotypes with IC90 values lower than 0.4 µg/ml. These data demonstrate that several of the isolated human antibodies have broad and potent neutralizing activity against antigenically divergent H5 pseudotypes.

TABLE 6

Neutralization of HA-pseudotypes (IC90, µg/ml) H5N1

| Ab | A/HK/ 491/97 | A/HK/ 213/03 | A/VN/ 1194/04 | A/VN/ 1203/04 | A/INDO/ 5/05 | A/WS/Mong/ 244/05 | A/Anhui/ 1/5 |
|---|---|---|---|---|---|---|---|
| FB54 | 0.021 | 0.033 | 0.036 | 0.028 | 0.084 | 0.066 | 0.059 |
| FB79 | 0.020 | 0.007 | 0.003 | 0.037 | 0.245 | 0.016 | 0.050 |
| FB118 | 0.028 | 0.007 | 0.027 | 0.062 | 0.316 | 0.060 | 0.119 |
| FB139 | 0.019 | 0.019 | 0.040 | 0.034 | 0.106 | 0.035 | 0.022 |
| FB179 | 0.107 | 0.144 | 0.125 | 0.133 | 0.933 | 0.384 | 0.242 |
| FB186 | 0.057 | 0.022 | 0.045 | 0.092 | 0.131 | 0.058 | 0.139 |
| FC6 | 0.081 | 0.077 | 0.061 | 0.096 | 0.242 | 0.073 | 0.112 |
| FC41 | 0.016 | 0.044 | 0.045 | 0.066 | 0.123 | 0.057 | 0.082 |
| FE9b | 0.014 | 0.155 | 0.097 | 0.028 | 0.235 | 0.018 | 0.034 |
| FE25 | 0.078 | 0.133 | 0.195 | 0.165 | 0.751 | 0.264 | 0.489 |
| FE43 | 0.053 | 0.070 | 0.061 | 0.146 | 0.390 | 0.186 | 0.137 |
| FE53 | 0.046 | 0.066 | 0.008 | 0.098 | 0.491 | 0.077 | 0.065 |
| FE54 | 0.044 | 0.105 | 0.036 | 0.093 | 4.412 | 0.025 | 0.058 |
| FG20 | 1.455 | 0.930 | 1.562 | 1.795 | 9.996 | 3.671 | 2.458 |
| FB15b | 0.344 | 0.888 | 0.102 | 0.340 | 18.29 | 0.518 | 1.099 |
| FB75 | 0.621 | 0.013 | 0.011 | 0.020 | 0.054 | 0.026 | 0.026 |
| FB110 | 3.620 | 0.013 | 0.018 | 0.017 | 0.066 | 0.060 | 0.037 |
| FB177 | 1.306 | 0.004 | 0.002 | 0.018 | 0.552 | 8.066 | 0.039 |
| FC1c | 0.042 | 0.729 | 0.493 | 0.057 | 0.359 | 0.073 | 0.112 |
| FE17 | 0.099 | 0.367 | 0.367 | 0.525 | >50 | 1.805 | >50 |
| FC54 | 0.724 | 0.982 | 0.369 | 0.912 | 4.540 | 1.130 | 0.932 |

The antibodies were next tested for their capacity to neutralize human and avian infectious influenza A viruses belonging to group 1 and group 2 subtypes (Table 7A, 7B). Most antibodies showed considerable breadth of viral neutralization, being able to neutralize two or more influenza A viruses belonging to group 1 subtype, namely H1N1, H2N2, H5N1, H6N1 and H9N2.

TABLE 7A

Neutralization of infectious viruses (IC50, µg/ml)

| | H1N1 | | | H2N2 | H5N1 | |
|---|---|---|---|---|---|---|
| Ab | A/NC/ 20/99 | A/SI/ 3/06 | A/PR/ 8/34 | A/JP/ 305/57 | A/VN/ 1203/04 | A/INDO/ 5/05 |
| FB54 | 50 | 9 | 9 | — | — | 16 |
| FB79 | 40 | 10 | 18 | 63 | — | 20 |
| FB118 | — | 16 | — | — | — | 20 |
| FB139 | 36 | 4 | 5 | 50 | 36 | 36 |
| FB179 | — | 31 | 36 | 63 | — | — |
| FB186 | 63 | 13 | 20 | — | — | 25 |
| FC6 | 40 | 18 | 16 | — | — | 31 |
| FC41 | 63 | 31 | 31 | 25 | 40 | 25 |
| FE9b | — | — | 36 | — | — | — |
| FE25 | — | — | 18 | — | — | 50 |
| FE43 | 40 | 9 | 4 | — | — | 25 |
| FE53 | 37 | 6 | — | — | — | — |
| FE54 | 20 | 40 | 18 | — | — | 63 |
| FG20 | — | — | 50 | — | — | — |
| FB15b | 36 | 8 | 13 | — | — | — |
| FB75 | 36 | 8 | 10 | — | 63 | 16 |
| FB110 | 22 | 5 | 6 | 7 | 36 | 22 |
| FB177 | 40 | 13 | 20 | 63 | — | 18 |
| FC1c | — | 10 | 9 | — | 63 | 16 |
| FE17 | 0.3 | <0.04 | 2 | — | 6 | — |
| FC54 | — | — | — | — | — | — |

The symbol — indicates that the antibody did not neutralize at the highest concentration tested.

TABLE 7B

Neutralization of infectious viruses (IC50, µg/ml)

| | H6N1 | H9N2 | | H7N3 | H7N7 |
|---|---|---|---|---|---|
| Ab | A/teal/HK/ WN312/97 | A/ck/HK/ G9/97 | A/HK/ 1073/99 | A/ck/BC/ CN-7/04 | A/NL/ 219/03 |
| FB54 | — | 9 | 36 | — | — |
| FB79 | — | — | — | — | — |
| FB118 | — | 36 | — | — | — |
| FB139 | — | 6 | 20 | — | — |
| FB179 | — | 13 | 25 | — | — |
| FB186 | — | 40 | — | — | — |
| FC6 | 63 | 9 | 36 | — | — |
| FC41 | 63 | 9 | 20 | — | — |
| FE9b | — | — | — | — | — |
| FE25 | — | 9 | 31 | — | — |

TABLE 7B-continued

Neutralization of infectious viruses (IC50, μg/ml)

| Ab | H6N1 A/teal/HK/ WN312/97 | H9N2 A/ck/HK/ G9/97 | H9N2 A/HK/ 1073/99 | H7N3 A/ck/BC/ CN-7/04 | H7N7 A/NL/ 219/03 |
|---|---|---|---|---|---|
| FE43 | 20 | 4 | 50 | — | — |
| FE53 | — | 2 | 8 | — | — |
| FE54 | — | — | — | — | — |
| FG20 | — | — | — | — | — |
| FB15b | — | — | — | — | — |
| FB75 | — | — | — | — | — |
| FB110 | — | — | — | — | — |
| FB177 | — | — | — | — | — |
| FC1c | — | 50 | — | — | — |
| FE17 | — | — | — | — | — |
| FC54 | — | — | — | — | — |

The symbol — indicates that the antibody did not neutralize at the highest concentration tested.

Three selected stem-specific (see below) antibodies (FE43, FC41 and FB110) and the globular head-specific (see below) antibody (FE17) were tested against a panel of human and animal H1N1 viruses spanning several decades of antigenic evolution and including the recent pandemic virus A/CA/07/09 (Table 8). FE17 neutralized four out of six viruses, and FB110, FC41 and FE43 neutralized all six H1N1 isolates, including the pandemic A/CA/07/09 strain. Taken together, these findings illustrate the capacity of the isolated heterosubtypic neutralizing antibodies to be insensitive to the antigenic evolution of influenza A virus.

TABLE 8

Neutralization of infectious viruses (IC50, μg/ml)

| Ab | H1N1 A/PR/ 8/34 | H1N1 A/swine/ Iowa/31 | H1N1 A/NJ/ 76 | H1N1 A/CA/ 07/09 | H5N1 A/VN/ 1203/04 |
|---|---|---|---|---|---|
| FC41 | 31.3 | 0.5 | 0.3 | 0.2 | >12 |
| FE43 | 1.5 | 3.0 | 9.0 | 4.0 | >50 |
| FB110 | 0.4 | 1.2 | 1.2 | 0.4 | >50 |
| FE17 | 1.0 | 0.1 | >50 | >50 | 6 |

Example 2

Antigenic Sites and VH-Gene Usage by Heterosubtypic Neutralizing Antibodies

In an attempt to understand whether the isolated antibodies bind an epitope located on HA1 or HA2, we performed Western blot (WB) analysis with recombinant HA from the H5N1 A/VN/1194/04 virus. None of the antibodies reacted in WB, suggesting that they may recognize a conformational epitope. We therefore evaluated antibody binding to HA-transfected (A/VN/1194/04) HEK293T cells before and after treatment at pH5.0 that triggers an irreversible conformational change in the HA molecule. With the single exception of FE17, all antibodies stained H5 transfected control cells, but failed to react with acid-treated cells. Without being bound by any particular theory regarding epitope binding, the results suggest that they bind to a pre-fusion determinant which is lost upon acidic treatment (Table 9).

To further explore the identity of the antigen sites to which the antibodies bind, we measured the capacity of the antibodies to interfere with the binding of reference antibodies of known epitope specificity: i) C179, a mouse monoclonal antibody that binds to an epitope in the stem of HA (Okuno et al., 1993), and ii) FLD21, a human H5 HA specific monoclonal antibody that binds to the HA globular head. ELISA plates were coated with recombinant trimeric H5 HA (A/VN/1203/04) and incubated with an excess of the human antibodies for one hour at room temperature, followed by the addition of limiting concentrations of C179 or FLD21 that were then detected using specific secondary reagents. With the single exception of FE17, all antibodies fully competed with C 179 for binding to the H5 HA, while they did not affect binding of FLD21 (Table 9). Reciprocally, FE17 competed with FLD21 for HA binding but did not affect C179 binding. These findings indicate that FE17 binds to an epitope in the globular head, while all the other heterosubtypic antibodies bind to epitopes located in the HA stem region that overlap with the C179 epitope on a H5 HA molecule in vitro.

TABLE 9

| Ab | HA[1] Binding Untreated | HA[1] Binding Acid-treated | Competition (%) C179 | Competition (%) FLD21 |
|---|---|---|---|---|
| FB54 | + | − | 100 | <20 |
| FB79 | + | − | 100 | <20 |
| FB118 | + | − | 100 | <20 |
| FB139 | + | − | 100 | <20 |
| FB179 | + | − | 100 | <20 |
| FB186 | + | − | 100 | <20 |
| FC6 | + | − | 100 | <20 |
| FC41 | + | − | 100 | <20 |
| FE9b | + | − | 100 | <20 |
| FE25 | + | − | 100 | <20 |
| FE43 | + | − | 100 | <20 |
| FE53 | + | − | 100 | <20 |
| FE54 | + | − | 100 | <20 |
| FG20 | + | − | 100 | <20 |
| FB15b | + | − | 100 | <20 |
| FB75 | + | − | 100 | <20 |
| FB110 | + | − | 100 | <20 |
| FB177 | + | − | 100 | <20 |
| FC1c | + | − | 100 | <20 |
| FE17 | + | + | <20 | 100 |
| FC54 | + | − | 100 | <20 |

[1]HA from H5N1 virus A/VN/1203/04

To further dissect the heterogeneity of the isolated heterosubtypic neutralizing antibodies we sequenced Ig genes. Fourteen antibodies used the VH1-69 germline sequence, which was paired with different VL (Table 10). The other antibodies used either VH3-23 paired with VL2-23 or VH4-39 paired with VL1-44.

TABLE 10

| Ab | Heavy chain, germline sequence | Light chain, germline sequence | Ab type |
|---|---|---|---|
| FB54 | IGHV 1-69*06 | IGKV 3-20*01 | 1 |
| FB79 | IGHV 1-69*06 | nd | 1 |
| FB118 | IGHV 1-69*01 | IGLV 2-8*01 | 1 |
| FB139 | IGHV 1-69*06 | IGKV 3-20*01 | 1 |
| FB179 | IGHV 1-69*01 | nd | 1 |
| FB186 | IGHV 1-69*06 | IGKV 3-20*01 | 1 |
| FC6 | IGHV 1-69*01 | IGKV 2D-29*01 | 1 |
| FC41 | IGHV 1-69*06 | IGKV 3-20*01 | 1 |
| FE9b | IGHV 1-69*06 | IGKV 3-20*01 | 1 |
| FE25 | IGHV 1-69*01 | IGKV 3-15*01 | 1 |
| FE43 | IGHV 1-69*01 | IGKV 2D-29*01 | 1 |
| FE53 | IGHV 1-69*06 | IGKV 1-33*01 | 1 |
| FE54 | IGHV 1-69*06 | IGKV 3-20*01 | 1 |
| FG20 | IGHV 1-69*06 | IGKV 2-14*01 | 1 |
| FB15b | IGHV 3-53*02 | IGLV 2-8*01 | 2 |

TABLE 10-continued

| Ab | Heavy chain, germline sequence | Light chain, germline sequence | Ab type |
|---|---|---|---|
| FB75 | IGHV 3-23*01 | IGLV 2-23*02 | 2 |
| FB110 | IGHV 3-23*01 | IGLV 2-23*02 | 2 |
| FB177 | IGHV 3-23*01 | nd | 2 |
| FC1c | IGHV 3-30*03 | nd | 2 |
| FE17 | IGHV 4-39*01 | IGLV 1-44*01 | 3 | nd, not done

Based on the reactivity pattern and the VH-gene usage the above results are consistent with the isolation of three types of heterosubtypic antibodies designated as Type 1, Type 2 and Type 3. Without being bound by any particular theory on germline usage with respect to epitope recognition or neutralization, Type 1 antibodies recognize conformational epitope(s) located in the HA stem region that are lost upon acidic treatment and use the VH1-69 germline sequence. Type 2 antibodies recognize acid-sensitive conformational epitope(s) located in the HA stem region but do not use the VH1-69 germline sequence. Type 3 antibodies, as exemplified by FE17, recognize an epitope in the HA globular head that is shared between H1 and some H5 subtypes. Type 1 and Type 2 antibodies showed very low hemagglutination inhibition titers against H1N1 viruses, consistent with the notion that these antibodies bind to the HA stem regions (Table 11). In contrast the globular head specific antibody showed potent hemagglutination inhibition.

TABLE 11

| | Hemagglutination inhibition titer | | | | |
|---|---|---|---|---|---|
| | H1N1 | | | | H5N1 |
| mAb | A/PR/ 8/34 | A/swine/ Iowa/31 | A/NJ/ 76 | A/CA/ 07/09 | A/VN/ 1203/04 |
| FC41 | <5 | 10 | <5 | 20 | <5 |
| FE43 | <5 | 20 | <5 | <5 | <5 |
| FB110 | 320 | 160 | 160 | 320 | 80 |
| FE17 | >1280 | >1280 | <5 | <5 | >1280 |

Example 3

Epitope Specificity of Heterosubtypic Neutralizing Antibodies

To map the epitopes recognized by the heterosubtypic neutralizing antibodies we attempted to isolate virus escape mutants using influenza virus A/SI/2/06. Seven escape mutants isolated in the presence of FE17 carried a point mutation in the globular head (S to N in position 145 of HA1, according to H3 numbering). This finding is consistent with the cross-competition data and with the failure of FE17 to bind to H5 from A/INDO/5/05 that carries a S to P substitution in the same position. In contrast, in spite of several attempts we failed to isolate escape mutants from FE43 and FB110. These findings suggest that the stem region recognized by the heterosubtypic antibodies are less prone to mutate without loss of viral fitness.

Example 4

Prophylactic Efficacy of Human Antibodies in Vivo

To determine whether the neutralizing activity displayed by the antibodies in vitro would be predictive of their prophylactic efficacy in vivo, BALB/c mice were passively immunized intraperitoneally (i.p.) with 25 or 2.5 mg/kg of FE17, FE43 or a control antibody and were challenged after 24 hours with 50 $MLD_{50}$ (fifty percent mouse lethal dose) of the following influenza viruses: H1N1 A/PR/8/34, H6N1 A/teal/HK/W312/97, H5N1 A/VN/1203/04, H5N1 A/INDO/5/05, or H7N7 A/NL/219/03. FE43 protected mice from lethal challenge with PR8 at either concentration tested, while FE17 conferred protection in a dose-dependent manner, affording 100% protection in animals that received 25 mg/kg of the antibody and 80% protection in animals that were injected with 2.5 mg/kg (FIG. 1A). Interestingly, despite the absence of detectable virus neutralizing activity in vitro, FE43 at 25 mg/kg protected all mice from the lethal Glade I H5N1 A/VN/1203/04 virus, while at 2.5 mg/kg afforded only partial protection (FIG. 1B). Both doses of FE17 protected mice from lethal H5N1 A/VN/1203/04 virus challenge as predicted by its neutralizing activity in vitro. After challenge with the Glade 2 H5N1 A/INDO/5/05 virus, protection was observed only with the highest dose of FE43 (FIG. 1C). Consistent with the neutralizing activity displayed in vitro, FE43 fully protected mice against challenge with lethal dose of the avian H6N1 A/teal/HK/W312/97 virus at both doses tested, whereas all mice injected with FE17 were not protected (FIG. 1D). As expected, none of the antibodies conferred protection against the lethal H7N7 A/NL/219/03 virus challenge (FIG. 1E).

To evaluate the in vivo neutralizing activity against the non-lethal H9N2 A/ck/HK/G9/97 virus, mice were injected i.p. either with FE43, FE17, a control antibody or a ferret hyper-immune serum and challenged 24 hours later with $10^5$ TCID50 of the H9N2 virus. Mice were sacrificed on day 4 p.i. and lungs were collected to measure the replicating viral titer. Consistent with the neutralizing activity demonstrated in vitro, mice that were injected with FE43 displayed 2-log viral replication reduction in their lungs, while no significant difference was observed with the control antibody (FIG. 1F).

REFERENCES

Okuno et al., (1993) Journal of Virology 67: 2552-2558.
Gerhard et al., (2006) Emerging Infectious Diseases 12: 569-574.
Gioia et al., (2008) Emerging Infectious Diseases 14: 121-128.
U.S. Pat. No. 3,766,162
U.S. Pat. No. 3,791,932
U.S. Pat. No. 3,817,837
U.S. Pat. No. 4,233,402
U.S. Pat. No. 4,676,980
U.S. Pat. No. 4,831,175
U.S. Pat. No. 5,595,721
WO00/52031
WO00/52473
U.S. Pat. No. 4,766,106
U.S. Pat. No. 4,179,337
U.S. Pat. No. 4,495,285
U.S. Pat. No. 4,609,546
Gabizon et al., (1982) Cancer Research 42:4734
Cafiso (1981) Biochem Biophys Acta 649:129
Szoka (1980) Ann. Rev. Biophys. Eng. 9:467
Poznansky et al., (1980) Drug Delivery Systems (R. L. Juliano, ed., Oxford, N.Y.) pp. 253-315
Poznansky (1984) Pharm Revs 36:277
Kohler, G. and Milstein, C,. 1975, Nature 256:495-497.
Kozbar et al., 1983, Immunology Today 4:72.
WO2004/076677

Chapter 4 of Kuby Immunology (4th edition, 2000; ASIN: 0716733315)
Jones et al., Biotechnol Prog 2003,19(1):163-8
Cho et al., Cytotechnology 2001,37:23-30
Cho et al., Biotechnol Prog 2003,19:229-32
U.S. Pat. No. 5,807,715
U.S. Pat. No. 6,300,104
Rowe et al., (1999) J Clin Microbiol 37(4):937-43.
Temperton, et al., (2005). Emerg Infect Dis 11, 411-416.
Smirnov et al., (2000). Arch Virol 145, 1733-1741.
Smirnov et al., (1999). Acta Virol 43, 237-244.
Simmons et al., (2007). PLoS Med 4, e178.
Traggiai et al., (2004). Nat Med 10, 871-875.

SEQ ID Number List

| SEQ ID NO | Description | Sequence |
|---|---|---|
| 1 | CDRH1 aa | GVTFSMYT |
| 2 | CDRH2 aa | IIPLFGTA |
| 3 | CDRH3 aa | ARAGTTLTRFNWFDP |
| 4 | CDRL1 aa | QTVSSSY |
| 5 | CDRL2 aa | GAS |
| 6 | CDRL3 aa | QQYGNSPYT |
| 7 | CDRH1 nuc | ggagtcaccttcagcatgtatact |
| 8 | CDRH2 nuc | atcatccctctctttggaacagca |
| 9 | CDRH3 nuc | gcgagagcggggactacattaactagatttaattggttcgaccccc |
| 10 | CDRL1 nuc | cagactgttagcagcagttac |
| 11 | CDRL2 nuc | ggtgcatcc |
| 12 | CDRL3 nuc | caacagtatggtaactcaccgtacact |
| 13 | heavy ch aa | QVQLVQSGAEVKKPGSSLKVSCKASGVTFSMYTISWVRQAPGQGLEWMGGIIPLFGTANYEQKFQGRVTITADTSTNTAYMELSSLRSEDTAVYYCARAGTTLTRFNWFDPWGQGTLVTVSS |
| 14 | light ch aa | EIVLTQSPGTLSLSPGERATLSCRASQTVSSSYLAWYQQKPGQAPRLLIYGASSRATGIPDRFSGSGSGTDFTLTISRLEPEDFAVYYCQQYGNSPYTFGQGTKLEIK |
| 15 | heavy ch nuc | caggtgcagctggtgcagtctggggctgagtgaagaagcctgggtcctcggtgaaggtctcctgcaaggcttctggagtcaccttcagcatgtatactatcagctgggtgcgccaggcccctggacaagggcttgagtggatggggagggatcatccctctctttggaacagcaaactacgaacagaagttccagggcagagtcacgattaccgcggacacatccacgaacacagcctatggagctgagcagcctgagatctgaggacacggccgtatattactgtgcgagagcggggactacattaactagatttaattggttcgaccctggggccagggaaccctcgtcaccgtctcctcag |
| 16 | light ch nuc | gaaattgtgttgacgcagtctccaggcacctgtctttgtctccaggggaaagagccacctctcctgcagggccagtcagactgttagcagcagttacttagcctggtaccagcagaaacctg |
| 17 | CDRH1 aa | GVTFSMYA |
| 18 | CDRH2 aa | IIPLFGTT |
| 19 | CDRH3 aa | ARAGTTVTRFNWFDP |
| 20 | CDRL1 aa | QSVSSSY |
| 21 | CDRL2 aa | DAS |
| 22 | CDRL3 aa | QQYGSSPYT |
| 23 | CDRH1 nuc | ggagtcaccttcagcatgtatgct |
| 24 | CDRH2 nuc | atcatccctctgtttggtacaaca |
| 25 | CDRH3 nuc | gcgagagcgggcactacagtaactagatttaactggttcgacccc |
| 26 | CDRL1 nuc | cagagtgttagcagcagttac |
| 27 | CDRL2 nuc | gatgcatcc |
| 28 | CDRL3 nuc | cagcagtatggtagttcaccgtacact |
| 29 | heavy ch aa | QVQLVQSGAEVKKAGSSVKVSCQSSGVTFSMYAVSWVRQAPGQGLEWMGGIIPLFGTTTYAQKFEGRLTITADTSTNMAYLELRSLRSEDTAVYFCARAGTTVTRFNWFDPWGQGTLVTVSS |
| 30 | light ch aa | EVVLTQSPGTLSLSPGQRATLSCRASQSVSSYLAWYQQKPGQAPRLLIYDASNRATGIPDRFSGSGSGTDFTLTISRLEPEDFAVYYCQQYGSSPYTFGQGTKLEIK |
| 31 | heavy ch nuc | caggtgcagttggtgcagtctggggctgagtgaagaaggctgggtcctcggtgaaagtttcgtgccagtcttctggagtcaccttcagcatgtatgctgtcagctgggtgcgccaggcccctggtcaagggcttgagtggatgggggggatcatccctctgtttggtacaacaacctacgcacagaagttcgagggcagactcaccattaccgcggacacatccacgaacatggcatacctggagctgcgcagcctgagatctgaagacacggccgtatatttctgtgcgagagcgggcactacagtaactagatttaactggttcgaccctgggccagggaaccctggtcaccgtctcctccg |
| 32 | light ch nuc | gaagttgtgttgacgcagtctccaggcacctgtctttgtctccagggcaaagagccacctctcctgcagggccagtcagagtgttagcagcagttacttagcctggtaccagcagaaacctggccaggctcccaggctcctcatctatgatgcatccaacagggccactggcatcccagacagattcagtggcagtgggtctgggacagacttcactctcaccatcagcagactggagcctgaagattttgcagtgtattactgtcagcagtatggtagttcaccgtacacttttggccaggggaccaagctggagatcaaac |

| SEQ ID NO | Description | Sequence |
|---|---|---|
| 33 | CDRH1 aa | GGTFNSHA |
| 34 | CDRH2 aa | IIPMFGTT |
| 35 | CDRH3 aa | ARGQRYYYDRDGMDV |
| 36 | CDRL1 aa | QSLLHSDGKTY |
| 37 | CDRL2 aa | EVF |
| 38 | CDRL3 aa | MQSLQLPLT |
| 39 | CDRH1 nuc | ggaggcaccttcaacagccatgct |
| 40 | CDRH2 nuc | attatccctatgtttggaacaaca |
| 41 | CDRH3 nuc | gcgcgagggcagaggtattactatgataggg acggtatggacgtc |
| 42 | CDRL1 nuc | cagagcctcctgcatagtgatggaaagacct at |
| 43 | CDRL2 nuc | gaagttttc |
| 44 | CDRL3 nuc | atgcaaagtttacaactccctctcact |
| 45 | heavy ch aa | QGQLVQSGAEVKKSGSSVKVSCKTSGGTFNS HAISWVRQAPGQGLEWIGGIIPMFGTTNYAQ KLKGRIAITADQLPTTAYLELSSLRSEDTAV YYCARGQRYYYDRDGMDVWGQGTMVTVSS |
| 46 | light ch aa | EIVMTQTPLSLSVTPGQPASISCRSSQSLLH SDGKTYLYWYLQKPGQPPQLLISEVFNRFSG VPDRFSGSGSGTDFTLKISRVEAEDVGVYYC MQSLQLPLTFGGGTKVEIK |
| 47 | heavy ch nuc | caggggcagctggtgcagtctggggctgagg tgaagaagtctgggtcctcggtgaaggtctc ctgcaagacatctggaggcaccttcaacagc catgctatcagctgggtccgacaggcccctg gacaagggcttgagtggatgggagggattat ccctatgtttggaacaacaaactacgcgcag aagttgaagggcagaatcgcgattaccgcgg accaactcccgaccacagcctacctggagct gagcagcctgagatctgaggacacggccgtc tattactgtgcgcagaggtattact atgatagggacggtatggacgtctggggcca agggaccatggtcaccgtctcctcag |
| 48 | light ch nuc | gagattgtgatgacccagactccactctctc tgtccgtcacccctggacagccggcctccat ctcctgcaggtctagtcagagcctcctgcat agtgatggaaagacctatttgtattggtacc tgcagaagccaggccagcctccacagctcct gatctctgaagttttcaaccggttctctgga gtgccagataggttcagtggtagcgggtcag ggacagatttcacactgaaaatcagccggt ggaggctgaggatgttggggtttattactgc atgcaaagtttacaactccctctcactttcg gcggagggaccaaggtggagatcaaac |
| 49 | CDRH1 aa | GGIFSPYA |
| 50 | CDRH2 aa | IIAIFGTT |
| 51 | CDRH3 aa | ARGGRYYVDYFDY |
| 52 | CDRL1 aa | QSISSGY |
| 53 | CDRL3 aa | QQYGTSPQT |
| 54 | CDRH1 nuc | ggaggcatcttcagtccgtatgct |
| 55 | CDRH2 nuc | atcatcgctatctttggtacaaca |
| 56 | CDRH3 nuc | gcgagaggcgggagatactacgtcgactact ttgactac |
| 57 | CDRL1 nuc | cagagtattagcagcggctac |
| 58 | CDRL2 nuc | ggtgcatca |
| 59 | CDRL3 nuc | cagcaatatggtacctcacctcagacg |
| 60 | heavy ch aa | QVQLVQPGAEVKKPGSSVKVSCKASGGIFSP YAISWVRQAPGQGLEWMGGIIAIFGTTNYAQ KFQGRVTITADKSTTTAYLELNSLRFEDTAV YYCARGGRYYVDYFDYWGQGTLVSVSS |
| 61 | light ch aa | EIVLTQSPGTLSVSPGERATLSCRASQSISS GYLAWYQQKPGQAPRLLIYGASSRATGIPDR FSGSGSGTDPFTLTISRLEPEDFAVYYCQQYG TSPQTFGQGTKVEIK |
| 62 | heavy ch nuc | caggtgcagctggtgcagcctggggctgagg taaagaagcctgggtcctcggtgaaggtctc ctgcaaggcttctggaggcatcttcagtccg tatgctatcagctgggtgcgacaggcccctg gacaagggcttgagtggatgggaggatcat cgctatctttggtacaacaaactacgcacag aagttccagggcagagtcaccattaccgcgg acaaatccacgaccacagcctatctggaact gaacagcctgagatttgaggacacggccgtc tattactgtgcgagaggcgggagatactacg tcgactactttgactactggggccagggaac cctggtcagcgtctcctcag |
| 63 | light ch nuc | gaaattgtgttgacgcagtctccaggcaccc tgtcggtgtctccaggggaaagagccaccct ctcctgcagggccagtcagagtattagcagc ggctacttagcctggtaccagcagaaacctg gccaggctcccaggctcctcatctatggtgc atcaagcagggccactggcatcccagacagg ttcagtggcagtgggtctgggacagacttca ctctcaccatcagcagactggagcctgaaga ttttgcagtgtattactgtcagcaatatggt acctcacctcagacgttcggccaagggacca aggtggaaatcaaac |
| 64 | CDRH1 aa | GGPFSGFA |
| 65 | CDRH2 aa | ISAVFGTA |
| 66 | CDRH3 aa | ARSGGYLPQNNWIDP |
| 67 | CDRL2 aa | EVS |
| 68 | CDRL3 aa | MQNILLPLT |
| 69 | CDRH1 nuc | ggaggccccttcagcggctttgct |
| 70 | CDRH2 nuc | atctccgctgtctttggcacagca |
| 71 | CDRH3 nuc | gcgagatcgggtggttatttacctcagaaca actggatcgaccc |
| 72 | CDRL2 nuc | gaagtttcc |

| SEQ ID NO | Description | Sequence |
|---|---|---|
| 73 | CDRL3 nuc | atgcaaaatatactacttccgctcact |
| 74 | heavy ch aa | QVHLVQSGAEVKKPGSSVRLSCSASGGPFSG FAISWLRQAPGQGLEWLGGISAVFGTATYAQ KFQGRVTITADQFTSTSHMDLSRLTYDDTAV YYCARSGGYLPQNNWIDPWGQGTLVIVSS |
| 75 | light ch aa | DIVMTQTPLSLSVTPGQPASISCKSSQSLLH SDGKTYLYWYLQKPGQSPQLLIYEVSNRFSG VPDRFSGSGSGTDFTLKISRVEAEDVGVYYC MQNILLPLTFGGGTKVEIK |
| 76 | heavy ch nuc | caggtgcacctggtgcagtctggggctgagg tgaagaagcctgggtcctcggtgaggctctc ttgctcggcttctggaggccccttcagcggc tttgctatcagctggctgcgacaggcccctg gacaagggcttgagtggttgggcgggatctc cgctgtctttggcacagcaacctacgcacag aagttccaggggagagtcaccattactgcgg accaattcacgagcacatctcacatggacct gagtagactgacatatgacgacacggccgtt tattactgtgcgagatcgggtggttatttac ctcagaacaactggatcgacccctggggcca gggaaccctggtcatcgtctcctcag |
| 77 | light ch nuc | gacattgtgatgacccagactccactctctc tgtccgtcacccctggacagccggcctccat ctcctgcaagtctagtcagagcctcctgcat agtgatggaaagacctatttgtattggtacc tgcagaagccaggccagtctccacaactcct gatctatgaagtttccaaccgcttctctgga gtgccagataggttcagtggcagcgggtcag ggacagatttcacactgaaaatcagcggggt ggaggctgaggatgttggtgttattactgc atgcaaaatatactacttccgctcactttcg cggagggaccaaggtggagatcaaac |
| 78 | CDRH1 aa | GVTSSNYP |
| 79 | CDRH2 aa | VLPLFGVT |
| 80 | CDRH3 aa | ARGKRPGYCSGGVCSSDYW |
| 81 | CDRL1 aa | QDISRY |
| 82 | CDRL3 aa | QQYGYLPLT |
| 83 | CDRH1 nuc | ggagtcacgtccagcaactatcct |
| 84 | CDRH2 nuc | gtcctcccttgtttggtgtaact |
| 85 | CDRH3 nuc | gcgcggggaagagacctggatattgttctg gtggtgtctgctcatccgactac |
| 86 | CDRL1 nuc | caggacattagcaggtat |
| 87 | CDRL2 nuc | gacgcatcc |
| 88 | CDRL3 nuc | caacagtatggctatctccctctcact |
| 89 | heavy ch aa | QVQLVQSGAEVKKPGSSVKVSCKASGVTSSN YPITWVRQAPGQGLEWMGGVLPLFGVTNYAQ KFQGRVTISADKSTNTAYMELSSLRSEDTAV YYCARGKRPGYCSGGVCSSDYWGQGTLVTVS S |
| 90 | light ch aa | DIQMTQSPSSLSASVGDRVSITCQASQDISR YLNWYQQKPGEAPKLLIYDASNLETGVPSRF SGSGSGTDFTFTISSLQPEDIATYFCQQYGY LPLTFGPGTKVDSK |
| 91 | heavy nuc | caggtacagctggtacagtctggggctgagg tgaagaagcctgggtcctcggtgaaggtctc ctgcaaggctcttggagtcacgtccagcaac tatcctataaacctgggtgcgacaggccctg gacaagggcttgagtggatgggaggggtcct cccctttgttggtgtaactaactacgcacag aagttccaggggcagagtcacgatttccgcgg acaaatccacgaacacagcctacatggagct gagcagccttagatctgaggacacggccgtg tattactgtgcgcggggaagagacctggat attgttctggtggtgtctgctcatccgacta ctggggccagggaaccctggtcaccgtctca tcag |
| 92 | light ch nuc | gacatccagatgacccagtctccttcttcct gtctgcatctgtaggagacagagtcagtat cacatgccaggcgagtcaggacattagcagg tatttaaattggtatcagcagaaaccagggg aagcccctaagctcctgatctacgacgcatc caatctggagacaggggtcccatcaaggttc agtggcagtggatctgggacagattttactt tcaccatcagcagcctgcagcctgaagatat tgcgacatatttctgtcaacagtatggctat ctccctctcactttcggccctgggaccaaag tggattccaaac |
| 93 | CDRH1 aa | GDSVTRGGFY |
| 94 | CDRH2 aa | IYYNYNI |
| 95 | CDRH3 aa | ARHYPYYDLPTGFYSQFDF |
| 96 | CDRL1 aa | GSNIGSNT |
| 97 | CDRL2 aa | TNN |
| 98 | CDRL3 aa | AAWDDSLNGQL |
| 99 | CDRH1 nuc | ggtgactccgtcaccagaggcggtttctac |
| 100 | CDRH2 nuc | atctattataattacaacatc |
| 101 | CDRH3 nuc | gcgagacattacccgtattatgatcttccga ctggttttatagtcagtttgacttc |
| 102 | CDRL1 nuc | ggctccaacatcggaagtaatact |
| 103 | CDRL2 nuc | actaataat |
| 104 | CDRL3 nuc | gcggcatgggatgacagcctcaatggtcagc tg |
| 105 | heavy ch aa | QPQLQESGPGLVRPSETLSLTCTVSGDSVTR GGFYWGWIRQPPGKGLEWIGSIYYNYNIYHS PSLKSRVSLSVDTSKNQVSLKLASVTAADTA VYYCARHYPYYDLPTGFYSQFDFWGQGTPVT VSS |
| 106 | light ch aa | QSVLTQPPSASGAPGQRVTLSCSGSGSNIGS NTVSWYQQLPGTAPKLLVFTNNQRPSGVPDR FSGSKSGTSASLAISGLQSEDEADYYCAAWD DSLNGQLFGGGTKLTVL |
| 107 | heavy ch nuc | cagccgcagctgcaggagtcgggcccaggac tggtgaggccttcggagaccctgtccctcac ctgcactgtctctggtgactccgtcaccaga |

SEQ ID Number List

| SEQ ID NO | Description | Sequence |
|---|---|---|
| | | ggcggtttctactggggctggatccgccagc ccccagggaaggggcttgagtggattgggag catctattataattacaacatctaccacagc ccgtccctcaagagtcgggtcagtttgtccg tagacacgtccaagaaccaggtctccctgaa gctgcctctgtgaccgccgcagacacggct gtgtattactgtgcgagacattacccgtatt atgatcttccgactggttttatagtcagtt tgacttctggggcagggaaccccggtcacc gtctcctcag |
| 108 | light ch nuc | cagtctgtgctgactcagccaccctcagcgt ctggggccccggcagagggtcaccctctc ttgttctggaagcggctccaacatcggaagt aatactgttagctggtaccagcaactcccag gaacggccccccaaactcctcgtctttactaa taatcagcggccctcaggggtccctgaccga ttctctggctccaagtctggcacctcagcct ccctggccatcagtgggctccagtctgaaga tgaggctgattattactgtgcggcatgggat gacagcctcaatggtcagctgttcggcggag ggaccaagctgaccgtcctgg |
| 109 | CDRH1 aa | GFTFSNYA |
| 110 | CDRH2 aa | INSGGGAT |
| 111 | CDRH3 aa | AKEGGNTIFGLVTMAYYFDS |
| 112 | CDRL1 aa | GSDVGSSNL |
| 113 | CDRL2 aa | EVT |
| 114 | CDRL3 aa | CSYAGSSSSRV |
| 115 | CDRH1 nuc | ggattcacctttagtaactatgcc |
| 116 | CDRH2 nuc | ataaatagtggcggtggtgccaca |
| 117 | CDRH3 nuc | gcgaaagagggcggaaatacgattttttggat tggttaccatggcgtactactttgactcc |
| 118 | CDRL1 nuc | ggaagtgatgttggagttctaacctt |
| 119 | CDRL2 nuc | gaggtcact |
| 120 | CDRL3 nuc | tgctcatatgcaggtagtagcagttccagag tc |
| 121 | heavy ch aa | EVQLLESGGGLVHPGGSLRLSCAASGFTFSN YAMSWVRQAPGKGLEWVSSINSGGGATYYAD SVKGRFTISRDNSKNTLSLQMNSLRAEDTAV YYCAKEGGNTIFGLVTMAYYFDSWGQGTLVT VSS |
| 122 | light ch aa | QSALTQPASVSGSPGQSITISCTGTGSDVGS SNLVSWYQQHPAKAPKLIIYEVTKRPSGVSN RFSGSKSGNTASLTISGLQAEDEADYYCCSY AGSSSSRVFGTGTKVTVL |
| 123 | heavy ch nuc | gaggtgcagttgttggaatctgggggaggcc tggtacaccctggggggtcactgagactctc ctgtgcagcctctggattcacctttagtaac tatgccatgagctgggtccgccaggctccag ggaagggggctggagtgggtctcaagtataaa tagtggcggtggtgccacatactacgcagac tccgtgaagggccggttcaccatctccagag acaattccaagaacacgctgtctctgcaaat gaacagcctgagagccgaggacacggccgta tattactgtgcgaaagagggcggaaatacga ttttttggattggttaccatggcgtactactt |

| SEQ ID NO | Description | Sequence |
|---|---|---|
| | | tgactcctggggccagggaaccctggtcacc gtctcctcag |
| 124 | light ch nuc | cagtctgccctgactcagcctgcctccgtgt ctgggtctcctggacagtcgatcaccatctc ctgcactggaaccggaagtgatgttgggagt tctaaccttgtctcctggtaccaacaacacc cagccaaggcccccaaactcataatttatga ggtcactaagcggccctcaggggtttctaat cgcttctctggctccaagtctggcaacacgg cctccctgacaatctctgggctccaggctga ggacgaggctgattattactgctgctcatat gcaggtagtagcagttccagagtcttcggaa ctgggaccaaggtcaccgtcctag |
| 125 | CDRH1 aa | GGIFISQA |
| 126 | CDRH2 aa | IIPMFGAT |
| 127 | CDRH3 aa | ARLGSGSYHNGPNWFDP |
| 128 | CDRH1 nuc | ggaggcatcttcatcagccaagct |
| 129 | CDRH2 nuc | atcatccctatgtttggtgcaact |
| 130 | CDRH3 nuc | gcgagactcggttcggggagttatcataacg gacccaactggttcgacccc |
| 131 | heavy ch aa | QVQLVQSGAEVKKPGSSVKVSCKASGGIFIS QAISWVRQAPGQGLEWMGGIIPMFGATNYAQ KFQGRVTITADKSTNTVYMELSSLTSEDTAV YYCARLGSGSYHNGPNWFDPWGQGTLVTVSS |
| 132 | heavy ch nuc | caggtgcagctggtgcagtctggggctgagg tgaagaagcctgggtcctcggtgaaggtctc ctgcaaggcttctggaggcatcttcatcagc caagctatcagctgggtgcgacaggcccctg gacaagggcttgagtggatgggagggatcat ccctatgtttggtgcaactaactacgcacag aagttccagggcagagtcacgattaccgcgg acaaatccacgaacacagtctacatggagct gagcagcctgacatctgaggacacggccgtg tattactgtgcgagactcggttcggggagtt atcataacggacccaactggttcgacccctg gggccagggaaccctggtcaccgtctcctca g |
| 133 | CDRH1 aa | GFTFSSYA |
| 134 | CDRH2 aa | ISYDGSNQ |
| 135 | CDRH3 aa | AKDPRIRHLLYFPFTSMIYFDY |
| 136 | CDRH1 nuc | ggattcaccttcagtagttatgcc |
| 137 | CDRH2 nuc | atatcatatgatggaagtaatcaa |
| 138 | CDRH3 nuc | gcgaaagaccccgtcttaggcacctgctat atttcccgtttacatctatgatttactttga ctac |
| 139 | heavy ch aa | QVQLVESGGGVVQPGRSLRLSCAVSGFTFSS YAMHWVRQAPGKGLEWVAVISYDGSNQYYAD SVKGRFTISRDNSKNTLYLQMNSLRAEDTAL YYCAKDPRLRHLLYFPFTSMIYFDYWGQGTL VTVSS |
| 140 | heavy ch nuc | caggtgcagctggtggagtctgggggaggcg tggtccagcctggggaggtccctgagactctc ctgtgcagtctctggattcaccttcagtagt tatgccatgcactgggtccgccaggctccag |

SEQ ID Number List

| SEQ ID NO | Description | Sequence |
|---|---|---|
| | | gcaaggggctggagtgggtggcagttatatc |
| | | atatgatggaagtaatcaatattatgcagac |
| | | tccgtgaagggccgattcaccatctccagag |
| | | acaattccaagaacacactatatctgcaaat |
| | | gaacagcctgagagctgaggacacggctttg |
| | | tattactgtgcgaaagaccccgtcttaggc |
| | | acctgctatatttcccgtttacatctatgat |
| | | ttactttgactactggggccagggaaccctg |
| | | gtcaccgtctcctcag |

The invention claimed is:

1. An isolated human antibody, or an antigen binding fragment thereof, that neutralizes infection of at least two different group 1 subtypes or at least two different group 2 subtypes of influenza A virus comprising the heavy chain CDR1, CDR2 and CDR3 and the light chain CDR1, CDR2, and CDR3 sequences as set forth in SEQ ID NOs: 1-6; 17-22; 33-38; 49-52, 5, 53; 64-66, 36, 67, 68; 78-81, 21, 82; 93-98; or 109-114; respectively.

2. The antibody of claim 1, or an antigen binding fragment thereof, comprising a heavy chain variable region having at least 80% sequence identity to the amino acid sequence of SEQ ID NO: 13 and a light chain variable region having at least 80% sequence identity to the amino acid sequence of SEQ ID NO: 14; or a heavy chain variable region having at least 80% sequence identity to the amino acid sequence of SEQ ID NO: 29 and a light chain variable region having at least 80% sequence identity to the amino acid sequence of SEQ ID NO: 30; or a heavy chain variable region having at least 80% sequence identity to the amino acid sequence of SEQ ID NO: 45 and a light chain variable region having at least 80% sequence identity to the amino acid sequence of SEQ ID NO: 46; or a heavy chain variable region having at least 80% sequence identity to the amino acid sequence of SEQ ID NO: 60 and a light chain variable region having at least 80% sequence identity to the amino acid sequence of SEQ ID NO: 61; or a heavy chain variable region having at least 80% sequence identity to the amino acid sequence of SEQ ID NO: 74 and a light chain variable region having at least 80% sequence identity to the amino acid sequence of SEQ ID NO: 75; or a heavy chain variable region having at least 80% sequence identity to the amino acid sequence of SEQ ID NO: 89 and a light chain variable region having at least 80% sequence identity to the amino acid sequence of SEQ ID NO: 90; or a heavy chain variable region having at least 80% sequence identity to the amino acid sequence of SEQ ID NO: 105 and a light chain variable region having at least 80% sequence identity to the amino acid sequence of SEQ ID NO: 106; or a heavy chain variable region having at least 80% sequence identity to the amino acid sequence of SEQ ID NO: 121 and a light chain variable region having at least 80% sequence identity to the amino acid sequence of SEQ ID NO: 122.

3. An isolated antibody, or an antigen binding fragment thereof, wherein the antibody comprises a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 45 and a light chain variable region comprising the amino acid sequence of SEQ ID NO: 46; or a heavy chain variable region comprising the amino acid sequence of SEQ ID NO: 60 and a light chain variable region comprising the amino acid sequence of SEQ ID NO: 61; or a heavy chain variable region comprising the amino acid sequence of SEQ ID NO: 74 and a light chain variable region comprising the amino acid sequence of SEQ ID NO: 75; or a heavy chain variable region comprising the amino acid sequence of SEQ ID NO: 89 and a light chain variable region comprising the amino acid sequence of SEQ ID NO: 90; or a heavy chain variable region comprising the amino acid sequence of SEQ ID NO: 105 and a light chain variable region comprising the amino acid sequence of SEQ ID NO: 106; or a heavy chain variable region comprising the amino acid sequence of SEQ ID NO: 121 and a light chain variable region comprising the amino acid sequence of SEQ ID NO: 122, and wherein the antibody neutralizes influenza A virus.

4. The antibody of claim 1, or an antigen binding fragment thereof, wherein the antibody is FC41, FE43, FB54, FB139, FC6, FE53, FB75, FB177, FB110 or FE17.

5. The antibody of claim 1, or an antigen binding fragment thereof, wherein the antibody is a monoclonal antibody, a purified antibody, an isolated antibody, a single chain antibody, Fab, Fab', F(ab')2, Fv or scFv.

6. An isolated antibody, or an antigen binding fragment thereof, that binds to the same epitope as the antibody of claim 1, wherein the antibody or antigen binding fragment thereof neutralizes influenza A virus.

7. An antibody, or antigen binding fragment thereof, expressed by immortalized B cell clone FB54, FB139, FC6, FC41, FE43, FE53, FE17, FB75, FB110, FB177, or FB79, wherein the antibody neutralizes influenza A virus.

8. A bacterial expression vector comprising a polynucleotide encoding the antibody of claim 1, or an antigen binding fragment thereof.

9. The bacterial expression vector of claim 8, wherein the polynucleotide sequence is at least 75% identical to the nucleic acid sequence of any one of SEQ ID NOs: 7-12, 15, 16, 23-28, 31, 32, 39-44, 47, 48, 54-59, 62, 63, 69-73, 76, 77, 83-88, 91, 92, 99-104, 107, 108, 115-120, 123, 124, 128-130, 132, 136-138, or 140.

10. A cell expressing the antibody of claim 1, or an antigen binding fragment thereof wherein said cell is selected from the group consisting of an immortalized B cell, a transformed B cell clone, an HEK293T cell, a CHO cell, an NSO cell, an isolated myeloma cell, and a hybridoma cell.

11. A cell comprising the bacterial expression vector of claim 8 wherein said cell is selected from the group consisting of an immortalized B cell, a transformed B cell clone, an HEK293T cell, a CHO cell, an NSO cell, an isolated myeloma cell, and a hybridoma cell.

12. A pharmaceutical composition comprising the antibody of claim 1, or an antigen binding fragment thereof, and a pharmaceutically acceptable diluent or carrier.

13. A pharmaceutical composition comprising a first antibody or an antigen binding fragment thereof, and a second antibody, or an antigen binding fragment thereof, wherein the first antibody is the antibody of claim 1, and the second antibody neutralizes influenza A virus infection.

14. A method of reducing influenza A virus infection, or lowering the risk of influenza A virus infection, comprising: administering to a subject in need thereof, a therapeutically effective amount of the antibody of claim 1, or an antigen binding fragment thereof.

* * * * *

SEQUENCE LISTING

<160> NUMBER OF SEQ ID NOS: 140

<210> SEQ ID NO 1
<211> LENGTH: 8
<212> TYPE: PRT
<213> ORGANISM: Homo sapiens

<400> SEQUENCE: 1

Gly Val Thr Phe Ser Met Tyr Thr
1               5

<210> SEQ ID NO 2
<211> LENGTH: 8
<212> TYPE: PRT
<213> ORGANISM: Homo sapiens

<400> SEQUENCE: 2

Ile Ile Pro Leu Phe Gly Thr Ala
1               5

<210> SEQ ID NO 3
<211> LENGTH: 15
<212> TYPE: PRT
<213> ORGANISM: Homo sapiens

<400> SEQUENCE: 3

Ala Arg Ala Gly Thr Thr Leu Thr Arg Phe Asn Trp Phe Asp Pro
1               5                   10                  15

<210> SEQ ID NO 4
<211> LENGTH: 7
<212> TYPE: PRT
<213> ORGANISM: Homo sapiens

<400> SEQUENCE: 4

Gln Thr Val Ser Ser Ser Tyr
1               5

<210> SEQ ID NO 5
<211> LENGTH: 3
<212> TYPE: PRT
<213> ORGANISM: Homo sapiens

<400> SEQUENCE: 5

Gly Ala Ser
1

<210> SEQ ID NO 6
<211> LENGTH: 9
<212> TYPE: PRT
<213> ORGANISM: Homo sapiens

-continued

```
<400> SEQUENCE: 6

Gln Gln Tyr Gly Asn Ser Pro Tyr Thr
1               5

<210> SEQ ID NO 7
<211> LENGTH: 24
<212> TYPE: DNA
<213> ORGANISM: Homo sapiens

<400> SEQUENCE: 7
ggagtcacct tcagcatgta tact                                              24

<210> SEQ ID NO 8
<211> LENGTH: 24
<212> TYPE: DNA
<213> ORGANISM: Homo sapiens

<400> SEQUENCE: 8
atcatccctc tctttggaac agca                                              24

<210> SEQ ID NO 9
<211> LENGTH: 45
<212> TYPE: DNA
<213> ORGANISM: Homo sapiens

<400> SEQUENCE: 9
gcgagagcgg ggactacatt aactagattt aattggttcg acccc                       45

<210> SEQ ID NO 10
<211> LENGTH: 21
<212> TYPE: DNA
<213> ORGANISM: Homo sapiens

<400> SEQUENCE: 10
cagactgtta gcagcagtta c                                                 21

<210> SEQ ID NO 11
<211> LENGTH: 9
<212> TYPE: DNA
<213> ORGANISM: Homo sapiens

<400> SEQUENCE: 11 ggtgcatcc                                                                9

<210> SEQ ID NO 12
<211> LENGTH: 27
<212> TYPE: DNA
<213> ORGANISM: Homo sapiens

<400> SEQUENCE: 12
caacagtatg gtaactcacc gtacact                                           27

<210> SEQ ID NO 13
<211> LENGTH: 122
<212> TYPE: PRT
<213> ORGANISM: Homo sapiens

<400> SEQUENCE: 13

Gln Val Gln Leu Val Gln Ser Gly Ala Glu Val Lys Lys Pro Gly Ser
1               5                   10                  15

Ser Leu Lys Val Ser Cys Lys Ala Ser Gly Val Thr Phe Ser Met Tyr
            20                  25                  30

Thr Ile Ser Trp Val Arg Gln Ala Pro Gly Gln Gly Leu Glu Trp Met
```

```
                35                  40                  45

Gly Gly Ile Ile Pro Leu Phe Gly Thr Ala Asn Tyr Glu Gln Lys Phe
 50                  55                  60

Gln Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Gly Thr Thr Leu Thr Arg Phe Asn Trp Phe Asp Pro Trp
                100                 105                 110

Gly Gln Gly Thr Leu Val Thr Val Ser Ser
            115                 120

<210> SEQ ID NO 14
<211> LENGTH: 108
<212> TYPE: PRT
<213> ORGANISM: Homo sapiens

<400> SEQUENCE: 14

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Thr Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Asn Ser Pro
                 85                  90                  95

Tyr Thr Phe Gly Gln Gly Thr Lys Leu Glu Ile Lys
            100                 105

<210> SEQ ID NO 15
<211> LENGTH: 367
<212> TYPE: DNA
<213> ORGANISM: Homo sapiens

<400> SEQUENCE: 15
caggtgcagc tggtgcagtc tggggctgag gtgaagaagc ctgggtcctc gttgaaggtc      60
tcctgcaagg cttctggagt caccttcagc atgtatacta tcagctgggt gcgccaggcc     120
cctggacaag gcttgagtg gatgggaggg atcatccctc tctttggaac agcaaactac     180
gaacagaagt tccagggcag agtcacgatt accgcggaca catccacgaa cacagcctac     240
atggagctga gcagcctgag atctgaggac acggccgtat attactgtgc gagagcgggg     300
actacattaa ctagatttaa ttggttcgac ccctggggcc agggaaccct cgtcaccgtc     360
tcctcag                                                              367

<210> SEQ ID NO 16
<211> LENGTH: 325
<212> TYPE: DNA
<213> ORGANISM: Homo sapiens

<400> SEQUENCE: 16
gaaattgtgt tgacgcagtc tccaggcacc ctgtctttgt ctccagggga aagagccacc      60
ctctcctgca gggccagtca gactgttagc agcagttact tagcctggta ccagcagaaa     120
```

```
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcaa cagtatggta actcaccgta cactttggc    300 cagggggacca agctggagat caaac                                         325
```

```
<210> SEQ ID NO 17
<211> LENGTH: 8
<212> TYPE: PRT
<213> ORGANISM: Homo sapiens

<400> SEQUENCE: 17

Gly Val Thr Phe Ser Met Tyr Ala
1               5

<210> SEQ ID NO 18
<211> LENGTH: 8
<212> TYPE: PRT
<213> ORGANISM: Homo sapiens

<400> SEQUENCE: 18

Ile Ile Pro Leu Phe Gly Thr Thr
1               5

<210> SEQ ID NO 19
<211> LENGTH: 15
<212> TYPE: PRT
<213> ORGANISM: Homo sapiens

<400> SEQUENCE: 19

Ala Arg Ala Gly Thr Thr Val Thr Arg Phe Asn Trp Phe Asp Pro
1               5                   10                  15

<210> SEQ ID NO 20
<211> LENGTH: 7
<212> TYPE: PRT
<213> ORGANISM: Homo sapiens

<400> SEQUENCE: 20

Gln Ser Val Ser Ser Ser Tyr
1               5

<210> SEQ ID NO 21
<211> LENGTH: 3
<212> TYPE: PRT
<213> ORGANISM: Homo sapiens

<400> SEQUENCE: 21

Asp Ala Ser
1

<210> SEQ ID NO 22
<211> LENGTH: 9
<212> TYPE: PRT
<213> ORGANISM: Homo sapiens

<400> SEQUENCE: 22

Gln Gln Tyr Gly Ser Ser Pro Tyr Thr
1               5

<210> SEQ ID NO 23
<211> LENGTH: 24
<212> TYPE: DNA
<213> ORGANISM: Homo sapiens
```

-continued

<210> SEQ ID NO 23
<211> LENGTH: 24
<212> TYPE: DNA
<213> ORGANISM: Homo sapiens

<400> SEQUENCE: 23
ggagtcacct tcagcatgta tgct                                         24

<210> SEQ ID NO 24
<211> LENGTH: 24
<212> TYPE: DNA
<213> ORGANISM: Homo sapiens

<400> SEQUENCE: 24
atcatccctc tgtttggtac aaca                                         24

<210> SEQ ID NO 25
<211> LENGTH: 45
<212> TYPE: DNA
<213> ORGANISM: Homo sapiens

<400> SEQUENCE: 25
gcgagagcgg gcactacagt aactagattt aactggttcg acccc                  45

<210> SEQ ID NO 26
<211> LENGTH: 21
<212> TYPE: DNA
<213> ORGANISM: Homo sapiens

<400> SEQUENCE: 26
cagagtgtta gcagcagtta c                                            21

<210> SEQ ID NO 27
<211> LENGTH: 9
<212> TYPE: DNA
<213> ORGANISM: Homo sapiens

<400> SEQUENCE: 27 gatgcatcc                                                           9

<210> SEQ ID NO 28
<211> LENGTH: 27
<212> TYPE: DNA
<213> ORGANISM: Homo sapiens

<400> SEQUENCE: 28
cagcagtatg gtagttcacc gtacact                                      27

<210> SEQ ID NO 29
<211> LENGTH: 122
<212> TYPE: PRT
<213> ORGANISM: Homo sapiens

<400> SEQUENCE: 29

Gln Val Gln Leu Val Gln Ser Gly Ala Glu Val Lys Lys Ala Gly Ser
1               5                   10                  15

Ser Val Lys Val Ser Cys Gln Ser Gly Val Thr Phe Ser Met Tyr
            20                  25                  30

Ala Val Ser Trp Val Arg Gln Ala Pro Gly Gln Gly Leu Glu Trp Met
        35                  40                  45

Gly Gly Ile Ile Pro Leu Phe Gly Thr Thr Tyr Ala Gln Lys Phe
    50                  55                  60

Glu Gly Arg Leu Thr Ile Thr Ala Asp Thr Ser Thr Asn Met Ala Tyr
65                  70                  75                  80

Leu Glu Leu Arg Ser Leu Arg Ser Glu Asp Thr Ala Val Tyr Phe Cys
                85                  90                  95

```
Ala Arg Ala Gly Thr Thr Val Thr Arg Phe Asn Trp Phe Asp Pro Trp
            100                 105                 110

Gly Gln Gly Thr Leu Val Thr Val Ser Ser
            115                 120

<210> SEQ ID NO 30
<211> LENGTH: 108
<212> TYPE: PRT
<213> ORGANISM: Homo sapiens

<400> SEQUENCE: 30

Glu Val Val Leu Thr Gln Ser Pro Gly Thr Leu Ser Leu Ser Pro Gly
1               5                   10                  15

Gln Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Asp Ala Ser Asn Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 31
<211> LENGTH: 367
<212> TYPE: DNA
<213> ORGANISM: Homo sapiens

<400> SEQUENCE: 31
caggtgcagt tggtgcagtc tggggctgag gtgaagaagg ctgggtcctc ggtgaaagtt      60
tcgtgccagt cttctggagt caccttcagc atgtatgctg tcagctgggt gcgccaggcc     120
cctggtcaag ggcttgagtg gatgggggg atcatccctc tgtttggtac aacaacctac     180
gcacagaagt tcgagggcag actcaccatt accgcggaca catccacgaa catggcatac     240
ctggagctgc gcagcctgag atctgaagac acggccgtat attttctgtg cgagagcggg     300
actacagtaa ctagatttaa ctggttcgac ccctggggcc agggaaccct ggtcaccgtc     360
tcctccg                                                              367

<210> SEQ ID NO 32
<211> LENGTH: 325
<212> TYPE: DNA
<213> ORGANISM: Homo sapiens

<400> SEQUENCE: 32
gaagttgtgt tgacgcagtc tccaggcacc ctgtctttgt ctccagggca agagccacc      60 ctctcctgca gggccagtca gagtgttagc agcagttact tagcctggta ccagcagaaa     120
cctggccagg ctcccaggct cctcatctat gatgcatcca acagggccac tggcatccca     180
gacagattca gtggcagtgg gtctgggaca gacttcactc tcaccatcag cagactggag     240
cctgaagatt ttgcagtgta ttactgtcag cagtatggta gttcaccgta cacttttggc     300
caggggacca agctggagat caaac                                          325

<210> SEQ ID NO 33
<211> LENGTH: 8
```

```
<212> TYPE: PRT
<213> ORGANISM: Homo sapiens

<400> SEQUENCE: 33

Gly Gly Thr Phe Asn Ser His Ala
1               5

<210> SEQ ID NO 34
<211> LENGTH: 8
<212> TYPE: PRT
<213> ORGANISM: Homo sapiens

<400> SEQUENCE: 34

Ile Ile Pro Met Phe Gly Thr Thr
1               5

<210> SEQ ID NO 35
<211> LENGTH: 15
<212> TYPE: PRT
<213> ORGANISM: Homo sapiens

<400> SEQUENCE: 35

Ala Arg Gly Gln Arg Tyr Tyr Tyr Asp Arg Asp Gly Met Asp Val
1               5                   10                  15

<210> SEQ ID NO 36
<211> LENGTH: 11
<212> TYPE: PRT
<213> ORGANISM: Homo sapiens

<400> SEQUENCE: 36

Gln Ser Leu Leu His Ser Asp Gly Lys Thr Tyr
1               5                   10

<210> SEQ ID NO 37
<211> LENGTH: 3
<212> TYPE: PRT
<213> ORGANISM: Homo sapiens

<400> SEQUENCE: 37

Glu Val Phe
1

<210> SEQ ID NO 38
<211> LENGTH: 9
<212> TYPE: PRT
<213> ORGANISM: Homo sapiens

<400> SEQUENCE: 38

Met Gln Ser Leu Gln Leu Pro Leu Thr
1               5

<210> SEQ ID NO 39
<211> LENGTH: 24
<212> TYPE: DNA
<213> ORGANISM: Homo sapiens

<400> SEQUENCE: 39
ggaggcacct tcaacagcca tgct                                         24

<210> SEQ ID NO 40
<211> LENGTH: 24
<212> TYPE: DNA
<213> ORGANISM: Homo sapiens

<400> SEQUENCE: 40
```

-continued attatcccta tgtttggaac aaca 24

<210> SEQ ID NO 41
<211> LENGTH: 45
<212> TYPE: DNA
<213> ORGANISM: Homo sapiens

<400> SEQUENCE: 41
gcgcgagggc agaggtatta ctatgatagg gacggtatgg acgtc 45

<210> SEQ ID NO 42
<211> LENGTH: 33
<212> TYPE: DNA
<213> ORGANISM: Homo sapiens

<400> SEQUENCE: 42
cagagcctcc tgcatagtga tggaaagacc tat 33

<210> SEQ ID NO 43
<211> LENGTH: 9
<212> TYPE: DNA
<213> ORGANISM: Homo sapiens

<400> SEQUENCE: 43 gaagttttc 9

<210> SEQ ID NO 44
<211> LENGTH: 27
<212> TYPE: DNA
<213> ORGANISM: Homo sapiens

<400> SEQUENCE: 44
atgcaaagtt tacaactccc tctcact 27

<210> SEQ ID NO 45
<211> LENGTH: 122
<212> TYPE: PRT
<213> ORGANISM: Homo sapiens

<400> SEQUENCE: 45

Gln Gly Gln Leu Val Gln Ser Gly Ala Glu Val Lys Lys Ser Gly Ser
1               5                   10                  15

Ser Val Lys Val Ser Cys Lys Thr Ser Gly Gly Thr Phe Asn Ser His
            20                  25                  30

Ala Ile Ser Trp Val Arg Gln Ala Pro Gly Gln Gly Leu Glu Trp Ile
        35                  40                  45

Gly Gly Ile Ile Pro Met Phe Gly Thr Thr Asn Tyr Ala Gln Lys Leu
    50                  55                  60

Lys Gly Arg Ile Ala Ile Thr Ala Asp Gln Leu Pro Thr Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Gln Arg Tyr Tyr Tyr Asp Arg Asp Gly Met Asp Val Trp
            100                 105                 110

Gly Gln Gly Thr Met Val Thr Val Ser Ser
        115                 120

<210> SEQ ID NO 46
<211> LENGTH: 112
<212> TYPE: PRT
<213> ORGANISM: Homo sapiens

<400> SEQUENCE: 46

Glu Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Ser Glu Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Gln Leu Pro Leu Thr Phe Gly Gly Gly Thr Lys Val Glu Ile Lys
            100                 105                 110

<210> SEQ ID NO 47
<211> LENGTH: 367
<212> TYPE: DNA
<213> ORGANISM: Homo sapiens

<400> SEQUENCE: 47
caggggcagc tggtgcagtc tggggctgag gtgaagaagt ctgggtcctc ggtgaaggtc      60
tcctgcaaga catctggagg caccttcaac agccatgcta tcagctgggt ccgacaggcc     120
cctggacaag ggcttgagtg gattggaggg attatcccta tgtttggaac aacaaactac     180
gcgcagaagt tgaagggcag aatcgcgatt accgcggacc aactcccgac acagcctac      240 ctggagctga gcagcctgag atctgaggac acggccgtct attactgtgc gcgagggcag     300
aggtattact atgatagggc ggtatggac gtctggggcc aagggaccat ggtcaccgtc     360
tcctcag                                                                367

<210> SEQ ID NO 48
<211> LENGTH: 337
<212> TYPE: DNA
<213> ORGANISM: Homo sapiens

<400> SEQUENCE: 48
gagattgtga tgacccagac tccactctct ctgtccgtca cccctggaca gccggcctcc      60
atctcctgca ggtctagtca gagcctcctg catagtgatg aaagaccta tttgtattgg    120 tacctgcaga agccaggcca gcctccacag ctcctgatct ctgaagtttt caaccggttc    180
tctggagtgc cagataggtt cagtggtagc gggtcaggga cagatttcac actgaaaatc    240
agccgggtgg aggctgagga tgttggggtt tattactgca tgcaaagttt acaactccct    300
ctcactttcg gcggagggac caaggtggag atcaaac                              337

<210> SEQ ID NO 49
<211> LENGTH: 8
<212> TYPE: PRT
<213> ORGANISM: Homo sapiens

<400> SEQUENCE: 49

Gly Gly Ile Phe Ser Pro Tyr Ala
1               5

<210> SEQ ID NO 50
<211> LENGTH: 8

```
<212> TYPE: PRT
<213> ORGANISM: Homo sapiens

<400> SEQUENCE: 50

Ile Ile Ala Ile Phe Gly Thr Thr
1               5

<210> SEQ ID NO 51
<211> LENGTH: 13
<212> TYPE: PRT
<213> ORGANISM: Homo sapiens

<400> SEQUENCE: 51

Ala Arg Gly Gly Arg Tyr Tyr Val Asp Tyr Phe Asp Tyr
1               5                   10

<210> SEQ ID NO 52
<211> LENGTH: 7
<212> TYPE: PRT
<213> ORGANISM: Homo sapiens

<400> SEQUENCE: 52

Gln Ser Ile Ser Ser Gly Tyr
1               5

<210> SEQ ID NO 53
<211> LENGTH: 9
<212> TYPE: PRT
<213> ORGANISM: Homo sapiens

<400> SEQUENCE: 53

Gln Gln Tyr Gly Thr Ser Pro Gln Thr
1               5

<210> SEQ ID NO 54
<211> LENGTH: 24
<212> TYPE: DNA
<213> ORGANISM: Homo sapiens

<400> SEQUENCE: 54
ggaggcatct tcagtccgta tgct                                          24

<210> SEQ ID NO 55
<211> LENGTH: 24
<212> TYPE: DNA
<213> ORGANISM: Homo sapiens

<400> SEQUENCE: 55
atcatcgcta tctttggtac aaca                                          24

<210> SEQ ID NO 56
<211> LENGTH: 39
<212> TYPE: DNA
<213> ORGANISM: Homo sapiens

<400> SEQUENCE: 56
gcgagaggcg ggagatacta cgtcgactac tttgactac                          39

<210> SEQ ID NO 57
<211> LENGTH: 21
<212> TYPE: DNA
<213> ORGANISM: Homo sapiens

<400> SEQUENCE: 57
cagagtatta gcagcggcta c                                             21
```

<210> SEQ ID NO 58
<211> LENGTH: 9
<212> TYPE: DNA
<213> ORGANISM: Homo sapiens

<400> SEQUENCE: 58 ggtgcatca                                                                  9

<210> SEQ ID NO 59
<211> LENGTH: 27
<212> TYPE: DNA
<213> ORGANISM: Homo sapiens

<400> SEQUENCE: 59
cagcaatatg gtacctcacc tcagacg                                             27

<210> SEQ ID NO 60
<211> LENGTH: 120
<212> TYPE: PRT
<213> ORGANISM: Homo sapiens

<400> SEQUENCE: 60

Gln Val Gln Leu Val Gln Pro Gly Ala Glu Val Lys Lys Pro Gly Ser
1               5                   10                  15

Ser Val Lys Val Ser Cys Lys Ala Ser Gly Ile Phe Ser Pro Tyr
            20                  25                  30

Ala Ile Ser Trp Val Arg Gln Ala Pro Gly Gln Gly Leu Glu Trp Met
        35                  40                  45

Gly Gly Ile Ile Ala Ile Phe Gly Thr Thr Asn Tyr Ala Gln Lys Phe
    50                  55                  60

Gln Gly Arg Val Thr Ile Thr Ala Asp Lys Ser Thr Thr Thr Ala Tyr
65                  70                  75                  80

Leu Glu Leu Asn Ser Leu Arg Phe Glu Asp Thr Ala Val Tyr Tyr Cys
                85                  90                  95

Ala Arg Gly Gly Arg Tyr Tyr Val Asp Tyr Phe Asp Tyr Trp Gly Gln
            100                 105                 110

Gly Thr Leu Val Ser Val Ser Ser
        115                 120

<210> SEQ ID NO 61
<211> LENGTH: 108
<212> TYPE: PRT
<213> ORGANISM: Homo sapiens

<400> SEQUENCE: 61

Glu Ile Val Leu Thr Gln Ser Pro Gly Thr Leu Ser Val Ser Pro Gly
1               5                   10                  15

Glu Arg Ala Thr Leu Ser Cys Arg Ala Ser Gln Ser Ile Ser Ser Gly
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Gln Thr Phe Gly Gln Gly Thr Lys Val Glu Ile Lys

<210> SEQ ID NO 62
<211> LENGTH: 361
<212> TYPE: DNA
<213> ORGANISM: Homo sapiens

<400> SEQUENCE: 62

```
caggtgcagc tggtgcagcc tggggctgag gtaaagaagc ctgggtcctc ggtgaaggtc      60
tcctgcaagg cttctggagg catcttcagt ccgtatgcta tcagctgggt gcgacaggcc     120
cctggacaag gcttgagtg gatgggaggg atcatcgcta tctttggtac aacaaactac     180
gcacagaagt tccagggcag agtcaccatt accgcggaca atccacgac acagcctat      240
ctggaactga acagcctgag atttgaggac acggccgtgt attactgtgc gagaggcggg     300
agatactacg tcgactactt tgactactgg ggccagggaa ccctggtcag cgtctcctca     360
g                                                                    361
```

<210> SEQ ID NO 63
<211> LENGTH: 325
<212> TYPE: DNA
<213> ORGANISM: Homo sapiens

<400> SEQUENCE: 63

```
gaaattgtgt tgacgcagtc tccaggcacc ctgtcggtgt ctccagggga aagagccacc      60
ctctcctgca gggccagtca gagtattagc agcggctact tagcctggta ccagcagaaa     120
cctggccagg ctcccaggct cctcatctat ggtgcatcaa gcagggccac tggcatccca     180
gacaggttca gtggcagtgg gtctgggaca gacttcactc tcaccatcag cagactggag     240
cctgaagatt ttgcagtgta ttactgtcag caatatggta cctcacctca gacgttcggc     300
caagggacca aggtggaaat caaac                                          325
```

<210> SEQ ID NO 64
<211> LENGTH: 8
<212> TYPE: PRT
<213> ORGANISM: Homo sapiens

<400> SEQUENCE: 64

Gly Gly Pro Phe Ser Gly Phe Ala
1               5

<210> SEQ ID NO 65
<211> LENGTH: 8
<212> TYPE: PRT
<213> ORGANISM: Homo sapiens

<400> SEQUENCE: 65

Ile Ser Ala Val Phe Gly Thr Ala
1               5

<210> SEQ ID NO 66
<211> LENGTH: 15
<212> TYPE: PRT
<213> ORGANISM: Homo sapiens

<400> SEQUENCE: 66

Ala Arg Ser Gly Gly Tyr Leu Pro Gln Asn Asn Trp Ile Asp Pro
1               5                   10                  15

<210> SEQ ID NO 67
<211> LENGTH: 3

```
<212> TYPE: PRT
<213> ORGANISM: Homo sapiens

<400> SEQUENCE: 67

Glu Val Ser
1

<210> SEQ ID NO 68
<211> LENGTH: 9
<212> TYPE: PRT
<213> ORGANISM: Homo sapiens

<400> SEQUENCE: 68

Met Gln Asn Ile Leu Leu Pro Leu Thr
1               5

<210> SEQ ID NO 69
<211> LENGTH: 24
<212> TYPE: DNA
<213> ORGANISM: Homo sapiens

<400> SEQUENCE: 69
ggaggcccct tcagcggctt tgct                                            24

<210> SEQ ID NO 70
<211> LENGTH: 24
<212> TYPE: DNA
<213> ORGANISM: Homo sapiens

<400> SEQUENCE: 70
atctccgctg tctttggcac agca                                            24

<210> SEQ ID NO 71
<211> LENGTH: 45
<212> TYPE: DNA
<213> ORGANISM: Homo sapiens

<400> SEQUENCE: 71
gcgagatcgg gtggttattt acctcagaac aactggatcg acccc                     45

<210> SEQ ID NO 72
<211> LENGTH: 9
<212> TYPE: DNA
<213> ORGANISM: Homo sapiens

<400> SEQUENCE: 72 gaagtttcc                                                              9

<210> SEQ ID NO 73
<211> LENGTH: 27
<212> TYPE: DNA
<213> ORGANISM: Homo sapiens

<400> SEQUENCE: 73
atgcaaaata tactacttcc gctcact                                         27

<210> SEQ ID NO 74
<211> LENGTH: 122
<212> TYPE: PRT
<213> ORGANISM: Homo sapiens

<400> SEQUENCE: 74

Gln Val His Leu Val Gln Ser Gly Ala Glu Val Lys Lys Pro Gly Ser
1               5                   10                  15
```

Ser Val Arg Leu Ser Cys Ser Ala Ser Gly Gly Pro Phe Ser Gly Phe
            20                  25                  30

Ala Ile Ser Trp Leu Arg Gln Ala Pro Gly Gln Gly Leu Glu Trp Leu
        35                  40                  45

Gly Gly Ile Ser Ala Val Phe Gly Thr Ala Thr Tyr Ala Gln Lys Phe
    50                  55                  60

Gln Gly Arg Val Thr Ile Thr Ala Asp Gln Phe Thr Ser Thr Ser His
65                  70                  75                  80

Met Asp Leu Ser Arg Leu Thr Tyr Asp Asp Thr Ala Val Tyr Tyr Cys
                85                  90                  95

Ala Arg Ser Gly Gly Tyr Leu Pro Gln Asn Asn Trp Ile Asp Pro Trp
            100                 105                 110

Gly Gln Gly Thr Leu Val Ile Val Ser Ser
        115                 120

<210> SEQ ID NO 75
<211> LENGTH: 112
<212> TYPE: PRT
<213> ORGANISM: Homo sapiens

<400> SEQUENCE: 75

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asn
                85                  90                  95

Ile Leu Leu Pro Leu Thr Phe Gly Gly Gly Thr Lys Val Glu Ile Lys
            100                 105                 110

<210> SEQ ID NO 76
<211> LENGTH: 367
<212> TYPE: DNA
<213> ORGANISM: Homo sapiens

<400> SEQUENCE: 76
caggtgcacc tggtgcagtc tggggctgag gtgaagaagc ctgggtcctc ggtgaggctc      60
tcttgctcgg cttctggagg ccccttcagc ggctttgcta tcagctggct gcgacaggcc     120
cctggacaag gcttgagtg gttgggcggg atctccgctg tctttggcac agcaacctac     180
gcacagaagt tccaggggag agtcaccatt actgcggacc aattcacgag cacatctcac     240
atggacctga gtagactgac atatgacgac acggccgttt attactgtgc gagatcgggt     300
ggttatttac ctcagaacaa ctggatcgac ccctggggcc agggaaccct ggtcatcgtc     360
tcctcag                                                               367

<210> SEQ ID NO 77
<211> LENGTH: 337
<212> TYPE: DNA
<213> ORGANISM: Homo sapiens

<400> SEQUENCE: 77

```
gacattgtga tgacccagac tccactctct ctgtccgtca cccctggaca gccggcctcc    60
atctcctgca agtctagtca gagcctcctg catagtgatg gaaagaccta tttgtattgg   120
tacctgcaga agccaggcca gtctccacaa ctcctgatct atgaagtttc caaccgcttc   180
tctggagtgc cagataggtt cagtggcagc gggtcaggga cagatttcac actgaaaatc   240
agccgggtgg aggctgagga tgttggtgtt tattactgca tgcaaaatat actacttccg   300
ctcactttcg gcggagggac caaggtggag atcaaac                            337
```

<210> SEQ ID NO 78
<211> LENGTH: 8
<212> TYPE: PRT
<213> ORGANISM: Homo sapiens

<400> SEQUENCE: 78

Gly Val Thr Ser Ser Asn Tyr Pro
1               5

<210> SEQ ID NO 79
<211> LENGTH: 8
<212> TYPE: PRT
<213> ORGANISM: Homo sapiens

<400> SEQUENCE: 79

Val Leu Pro Leu Phe Gly Val Thr
1               5

<210> SEQ ID NO 80
<211> LENGTH: 19
<212> TYPE: PRT
<213> ORGANISM: Homo sapiens

<400> SEQUENCE: 80

Ala Arg Gly Lys Arg Pro Gly Tyr Cys Ser Gly Gly Val Cys Ser Ser
1               5                   10                  15

Asp Tyr Trp

<210> SEQ ID NO 81
<211> LENGTH: 6
<212> TYPE: PRT
<213> ORGANISM: Homo sapiens

<400> SEQUENCE: 81

Gln Asp Ile Ser Arg Tyr
1               5

<210> SEQ ID NO 82
<211> LENGTH: 9
<212> TYPE: PRT
<213> ORGANISM: Homo sapiens

<400> SEQUENCE: 82

Gln Gln Tyr Gly Tyr Leu Pro Leu Thr
1               5

<210> SEQ ID NO 83
<211> LENGTH: 24
<212> TYPE: DNA
<213> ORGANISM: Homo sapiens

<400> SEQUENCE: 83
ggagtcacgt ccagcaacta tcct                                           24

```
<210> SEQ ID NO 84
<211> LENGTH: 24
<212> TYPE: DNA
<213> ORGANISM: Homo sapiens

<400> SEQUENCE: 84 gtcctcccttt tgtttggtgt aact                                          24

<210> SEQ ID NO 85
<211> LENGTH: 54
<212> TYPE: DNA
<213> ORGANISM: Homo sapiens

<400> SEQUENCE: 85
gcgcggggga agagacctgg atattgttct ggtggtgtct gctcatccga ctac           54

<210> SEQ ID NO 86
<211> LENGTH: 18
<212> TYPE: DNA
<213> ORGANISM: Homo sapiens

<400> SEQUENCE: 86
caggacatta gcaggtat                                                  18

<210> SEQ ID NO 87
<211> LENGTH: 9
<212> TYPE: DNA
<213> ORGANISM: Homo sapiens

<400> SEQUENCE: 87 gacgcatcc                                                             9

<210> SEQ ID NO 88
<211> LENGTH: 27
<212> TYPE: DNA
<213> ORGANISM: Homo sapiens

<400> SEQUENCE: 88
caacagtatg gctatctccc tctcact                                        27

<210> SEQ ID NO 89
<211> LENGTH: 125
<212> TYPE: PRT
<213> ORGANISM: Homo sapiens

<400> SEQUENCE: 89
```

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Ser Ser Asn Tyr
            20                  25                  30

Pro Ile Thr Trp Val Arg Gln Ala Pro Gly Gln Gly Leu Glu Trp Met
        35                  40                  45

Gly Gly Val Leu Pro Leu Phe Gly Val Thr Asn Tyr Ala Gln Lys Phe
    50                  55                  60

Gln Gly Arg Val Thr Ile Ser Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Pro Gly Tyr Cys Ser Gly Gly Val Cys Ser Ser
            100                 105                 110

Asp Tyr Trp Gly Gln Gly Thr Leu Val Thr Val Ser Ser
        115                 120                 125

<210> SEQ ID NO 90
<211> LENGTH: 107
<212> TYPE: PRT
<213> ORGANISM: Homo sapiens

<400> SEQUENCE: 90

Asp Ile Gln Met Thr Gln Ser Pro Ser Ser Leu Ser Ala Ser Val Gly
1               5                   10                  15
Asp Arg Val Ser Ile Thr Cys Gln Ala Ser Gln Asp Ile Ser Arg Tyr
            20                  25                  30
Leu Asn Trp Tyr Gln Gln Lys Pro Gly Glu Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Phe Cys Gln Gln Tyr Gly Tyr Leu Pro Leu
                85                  90                  95
Thr Phe Gly Pro Gly Thr Lys Val Asp Ser Lys
            100                 105

<210> SEQ ID NO 91
<211> LENGTH: 376
<212> TYPE: DNA
<213> ORGANISM: Homo sapiens

<400> SEQUENCE: 91
caggtacagc tggtacagtc tggggctgag gtgaagaagc ctgggtcctc ggtgaaggtc        60
tcctgcaagg cttctggagt cacgtccagc aactatccta aacctgggt gcgacaggcc       120 cctggacaag gacttgagtg gatgggaggg gtcctcccct tgtttggtgt aactaactac       180
gcacagaagt tccagggcag agtcacgatt tccgcggaca aatccacgaa acacagcctac      240 atggagctga gcagccttag atctgaggac acggccgtgt attactgtgc gcggggaag       300 agacctggat attgttctgg tggtgtctgc tcatccgact actggggcca gggaaccctg       360
gtcaccgtct catcag                                                      376

<210> SEQ ID NO 92
<211> LENGTH: 322
<212> TYPE: DNA
<213> ORGANISM: Homo sapiens

<400> SEQUENCE: 92
gacatccaga tgacccagtc tccttcttcc ttgtctgcat ctgtaggaga cagagtcagt        60
atcacatgcc aggcgagtca ggacattagc aggtatttaa attggtatca gcagaaacca       120
ggggaagccc ctaagctcct gatctacgac gcatccaatc tggagacagg gtcccatca       180 aggttcagtg gcagtggatc tgggacagat tttactttca ccatcagcag cctgcagcct       240
gaagatattg cgacatattt ctgtcaacag tatggctatc tccctctcac tttcggccct       300
gggaccaaag tggattccaa ac                                               322

<210> SEQ ID NO 93
<211> LENGTH: 10
<212> TYPE: PRT
<213> ORGANISM: Homo sapiens

<400> SEQUENCE: 93

```
Gly Asp Ser Val Thr Arg Gly Gly Phe Tyr
1               5                   10

<210> SEQ ID NO 94
<211> LENGTH: 7
<212> TYPE: PRT
<213> ORGANISM: Homo sapiens

<400> SEQUENCE: 94

Ile Tyr Tyr Asn Tyr Asn Ile
1               5

<210> SEQ ID NO 95
<211> LENGTH: 19
<212> TYPE: PRT
<213> ORGANISM: Homo sapiens

<400> SEQUENCE: 95

Ala Arg His Tyr Pro Tyr Tyr Asp Leu Pro Thr Gly Phe Tyr Ser Gln
1               5                   10                  15

Phe Asp Phe

<210> SEQ ID NO 96
<211> LENGTH: 8
<212> TYPE: PRT
<213> ORGANISM: Homo sapiens

<400> SEQUENCE: 96

Gly Ser Asn Ile Gly Ser Asn Thr
1               5

<210> SEQ ID NO 97
<211> LENGTH: 3
<212> TYPE: PRT
<213> ORGANISM: Homo sapiens

<400> SEQUENCE: 97

Thr Asn Asn
1

<210> SEQ ID NO 98
<211> LENGTH: 11
<212> TYPE: PRT
<213> ORGANISM: Homo sapiens

<400> SEQUENCE: 98

Ala Ala Trp Asp Asp Ser Leu Asn Gly Gln Leu
1               5                   10

<210> SEQ ID NO 99
<211> LENGTH: 30
<212> TYPE: DNA
<213> ORGANISM: Homo sapiens

<400> SEQUENCE: 99
ggtgactccg tcaccagagg cggtttctac                               30

<210> SEQ ID NO 100
<211> LENGTH: 21
<212> TYPE: DNA
<213> ORGANISM: Homo sapiens

<400> SEQUENCE: 100
atctattata attacaacat c                                        21
```

<210> SEQ ID NO 101
<211> LENGTH: 57
<212> TYPE: DNA
<213> ORGANISM: Homo sapiens

<400> SEQUENCE: 101
gcgagacatt acccgtatta tgatcttccg actggttttt atagtcagtt tgacttc        57

<210> SEQ ID NO 102
<211> LENGTH: 24
<212> TYPE: DNA
<213> ORGANISM: Homo sapiens

<400> SEQUENCE: 102
ggctccaaca tcggaagtaa tact        24

<210> SEQ ID NO 103
<211> LENGTH: 9
<212> TYPE: DNA
<213> ORGANISM: Homo sapiens

<400> SEQUENCE: 103 actaataat        9

<210> SEQ ID NO 104
<211> LENGTH: 33
<212> TYPE: DNA
<213> ORGANISM: Homo sapiens

<400> SEQUENCE: 104
gcggcatggg atgacagcct caatggtcag ctg        33

<210> SEQ ID NO 105
<211> LENGTH: 127
<212> TYPE: PRT
<213> ORGANISM: Homo sapiens

<400> SEQUENCE: 105

Gln Pro Gln Leu Gln Glu Ser Gly Pro Gly Leu Val Arg Pro Ser Glu
1               5                   10                  15

Thr Leu Ser Leu Thr Cys Thr Val Ser Gly Asp Ser Val Thr Arg Gly
            20                  25                  30

Gly Phe Tyr Trp Gly Trp Ile Arg Gln Pro Pro Gly Lys Gly Leu Glu
        35                  40                  45

Trp Ile Gly Ser Ile Tyr Tyr Asn Tyr Asn Ile Tyr His Ser Pro Ser
    50                  55                  60

Leu Lys Ser Arg Val Ser Leu Ser Val Asp Thr Ser Lys Asn Gln Val
65                  70                  75                  80

Ser Leu Lys Leu Ala Ser Val Thr Ala Ala Asp Thr Ala Val Tyr Tyr
                85                  90                  95

Cys Ala Arg His Tyr Pro Tyr Tyr Asp Leu Pro Thr Gly Phe Tyr Ser
            100                 105                 110

Gln Phe Asp Phe Trp Gly Gln Gly Thr Pro Val Thr Val Ser Ser
        115                 120                 125

<210> SEQ ID NO 106
<211> LENGTH: 110
<212> TYPE: PRT
<213> ORGANISM: Homo sapiens

<400> SEQUENCE: 106

```
Gln Ser Val Leu Thr Gln Pro Pro Ser Ala Ser Gly Ala Pro Gly Gln
 1               5                  10                  15

Arg Val Thr Leu Ser Cys Ser Gly Ser Ser Asn Ile Gly Ser Asn
             20                  25                  30

Thr Val Ser Trp Tyr Gln Gln Leu Pro Gly Thr Ala Pro Lys Leu Leu
             35                  40                  45

Val Phe Thr Asn Asn Gln Arg Pro Ser Gly Val Pro Asp Arg Phe Ser
         50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                 85                  90                  95

Asn Gly Gln Leu Phe Gly Gly Gly Thr Lys Leu Thr Val Leu
                100                 105                 110

<210> SEQ ID NO 107
<211> LENGTH: 382
<212> TYPE: DNA
<213> ORGANISM: Homo sapiens

<400> SEQUENCE: 107
cagccgcagc tgcaggagtc gggcccagga ctggtgaggc cttcggagac cctgtccctc      60
acctgcactg tctctggtga ctccgtcacc agaggcggtt tctactgggg ctggatccgc     120
cagcccccag ggaaggggct gagtggattg ggagcatct attataatta caacatctac     180
cacagcccgt ccctcaagag tcgggtcagt ttgtccgtag acacgtccaa gaaccaggtc     240
tccctgaagc tggcctctgt gaccgccgca gacacggctg tgtattactg tgcgagacat     300
tacccgtatt atgatcttcc gactggtttt tatagtcagt ttgacttctg gggccaggga     360
accccggtca ccgtctcctc ag                                              382

<210> SEQ ID NO 108
<211> LENGTH: 331
<212> TYPE: DNA
<213> ORGANISM: Homo sapiens

<400> SEQUENCE: 108
cagtctgtgc tgactcagcc accctcagcg tctggggccc ccggccagag ggtcaccctc      60
tcttgttctg gaagcggctc caacatcgga agtaatactg ttagctggta ccagcaactc     120
ccaggaacgg cccccaaact cctcgtcttt actaataatc agcggccctc aggggtccct     180
gaccgattct ctggctccaa gtctggcacc tcagcctccc tggccatcag tgggctccag     240
tctgaagatg aggctgatta ttactgtgcg gcatgggatg acagcctcaa tggtcagctg     300
ttcggcggag ggaccaagct gaccgtcctg g                                    331

<210> SEQ ID NO 109
<211> LENGTH: 8
<212> TYPE: PRT
<213> ORGANISM: Homo sapiens

<400> SEQUENCE: 109

Gly Phe Thr Phe Ser Asn Tyr Ala
 1               5

<210> SEQ ID NO 110
<211> LENGTH: 8
<212> TYPE: PRT
<213> ORGANISM: Homo sapiens
```

```
<400> SEQUENCE: 110

Ile Asn Ser Gly Gly Gly Ala Thr
1               5

<210> SEQ ID NO 111
<211> LENGTH: 20
<212> TYPE: PRT
<213> ORGANISM: Homo sapiens

<400> SEQUENCE: 111

Ala Lys Glu Gly Gly Asn Thr Ile Phe Gly Leu Val Thr Met Ala Tyr
1               5                   10                  15

Tyr Phe Asp Ser
            20

<210> SEQ ID NO 112
<211> LENGTH: 9
<212> TYPE: PRT
<213> ORGANISM: Homo sapiens

<400> SEQUENCE: 112

Gly Ser Asp Val Gly Ser Ser Asn Leu
1               5

<210> SEQ ID NO 113
<211> LENGTH: 3
<212> TYPE: PRT
<213> ORGANISM: Homo sapiens

<400> SEQUENCE: 113

Glu Val Thr
1

<210> SEQ ID NO 114
<211> LENGTH: 11
<212> TYPE: PRT
<213> ORGANISM: Homo sapiens

<400> SEQUENCE: 114

Cys Ser Tyr Ala Gly Ser Ser Ser Ser Arg Val
1               5                   10

<210> SEQ ID NO 115
<211> LENGTH: 24
<212> TYPE: DNA
<213> ORGANISM: Homo sapiens

<400> SEQUENCE: 115
ggattcacct ttagtaacta tgcc                                          24

<210> SEQ ID NO 116
<211> LENGTH: 24
<212> TYPE: DNA
<213> ORGANISM: Homo sapiens

<400> SEQUENCE: 116
ataaatagtg gcggtggtgc caca                                          24

<210> SEQ ID NO 117
<211> LENGTH: 60
<212> TYPE: DNA
<213> ORGANISM: Homo sapiens

<400> SEQUENCE: 117
```
gcgaaagagg gcggaaatac gattttgga ttggttacca tggcgtacta ctttgactcc    60

<210> SEQ ID NO 118
<211> LENGTH: 27
<212> TYPE: DNA
<213> ORGANISM: Homo sapiens

<400> SEQUENCE: 118
ggaagtgatg ttgggagttc taacctt    27

<210> SEQ ID NO 119
<211> LENGTH: 9
<212> TYPE: DNA
<213> ORGANISM: Homo sapiens

<400> SEQUENCE: 119 gaggtcact    9

<210> SEQ ID NO 120
<211> LENGTH: 33
<212> TYPE: DNA
<213> ORGANISM: Homo sapiens

<400> SEQUENCE: 120
tgctcatatg caggtagtag cagttccaga gtc    33

<210> SEQ ID NO 121
<211> LENGTH: 127
<212> TYPE: PRT
<213> ORGANISM: Homo sapiens

<400> SEQUENCE: 121

Glu Val Gln Leu Leu Glu Ser Gly Gly Gly Leu Val His Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Asn Ser Gly Gly Gly Ala Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Glu Gly Gly Asn Thr Ile Phe Gly Leu Val Thr Met Ala Tyr
            100                 105                 110

Tyr Phe Asp Ser Trp Gly Gln Gly Thr Leu Val Thr Val Ser Ser
        115                 120                 125

<210> SEQ ID NO 122
<211> LENGTH: 111
<212> TYPE: PRT
<213> ORGANISM: Homo sapiens

<400> SEQUENCE: 122

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Ser
            20                  25                  30

Asn Leu Val Ser Trp Tyr Gln Gln His Pro Ala Lys Ala Pro Lys Leu
        35                  40                  45

```
Ile Ile Tyr Glu Val Thr Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Ser Ser Arg Val Phe Gly Thr Gly Thr Lys Val Thr Val Leu
            100                 105                 110

<210> SEQ ID NO 123
<211> LENGTH: 382
<212> TYPE: DNA
<213> ORGANISM: Homo sapiens

<400> SEQUENCE: 123
gaggtgcagt tgttggaatc tgggggaggc ctggtacacc ctgggggtc actgagactc      60 tcctgtgcag cctctggatt cacctttagt aactatgcca tgagctgggt ccgccaggct    120
ccagggaagg gctggagtg gtctcaagt ataaatagtg gcggtggtgc cacatactac      180
gcagactccg tgaagggccg gttcaccatc tccagagaca attccaagaa cacgctgtct    240
ctgcaaatga acagcctgag agccgaggac acggccgtat attactgtgc gaaagagggc    300
ggaaatacga ttttggatt ggttaccatg gcgtactact ttgactcctg gggccaggga    360
accctggtca ccgtctcctc ag                                             382

<210> SEQ ID NO 124
<211> LENGTH: 334
<212> TYPE: DNA
<213> ORGANISM: Homo sapiens

<400> SEQUENCE: 124
cagtctgccc tgactcagcc tgcctccgtg tctgggtctc ctggacagtc gatcaccatc      60
tcctgcactg gaaccggaag tgatgttggg agttctaacc ttgtctcctg gtaccaacaa    120
cacccagcca aggccccaa actcataatt tatgaggtca ctaagcggcc ctcagggggt    180
tctaatcgct tctctggctc caagtctggc aacacggcct ccctgacaat ctctggactc    240
caggctgagg acgaggctga ttattactgc tgctcatatg caggtagtag cagttccaga    300
gtcttcggaa ctgggaccaa ggtcaccgtc ctag                                334

<210> SEQ ID NO 125
<211> LENGTH: 8
<212> TYPE: PRT
<213> ORGANISM: Homo sapiens

<400> SEQUENCE: 125

Gly Gly Ile Phe Ile Ser Gln Ala
1               5

<210> SEQ ID NO 126
<211> LENGTH: 8
<212> TYPE: PRT
<213> ORGANISM: Homo sapiens

<400> SEQUENCE: 126

Ile Ile Pro Met Phe Gly Ala Thr
1               5

<210> SEQ ID NO 127
<211> LENGTH: 17
```

<212> TYPE: PRT
<213> ORGANISM: Homo sapiens

<400> SEQUENCE: 127

Ala Arg Leu Gly Ser Gly Ser Tyr His Asn Gly Pro Asn Trp Phe Asp
1               5                   10                  15

Pro

<210> SEQ ID NO 128
<211> LENGTH: 24
<212> TYPE: DNA
<213> ORGANISM: Homo sapiens

<400> SEQUENCE: 128
ggaggcatct tcatcagcca agct                                              24

<210> SEQ ID NO 129
<211> LENGTH: 24
<212> TYPE: DNA
<213> ORGANISM: Homo sapiens

<400> SEQUENCE: 129
atcatcccta tgtttggtgc aact                                              24

<210> SEQ ID NO 130
<211> LENGTH: 51
<212> TYPE: DNA
<213> ORGANISM: Homo sapiens

<400> SEQUENCE: 130
gcgagactcg gttcggggag ttatcataac ggacccaact ggttcgaccc c                51

<210> SEQ ID NO 131
<211> LENGTH: 124
<212> TYPE: PRT
<213> ORGANISM: Homo sapiens

<400> SEQUENCE: 131

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ile Ser Gln
                20                  25                  30

Ala Ile Ser Trp Val Arg Gln Ala Pro Gly Gln Gly Leu Glu Trp Met
            35                  40                  45

Gly Gly Ile Ile Pro Met Phe Gly Ala Thr Asn Tyr Ala Gln Lys Phe
        50                  55                  60

Gln Gly Arg Val Thr Ile Thr Ala Asp Lys Ser Thr Asn Thr Val Tyr
65                  70                  75                  80

Met Glu Leu Ser Ser Leu Thr Ser Glu Asp Thr Ala Val Tyr Tyr Cys
                85                  90                  95

Ala Arg Leu Gly Ser Gly Ser Tyr His Asn Gly Pro Asn Trp Phe Asp
                100                 105                 110

Pro Trp Gly Gln Gly Thr Leu Val Thr Val Ser Ser
            115                 120

<210> SEQ ID NO 132
<211> LENGTH: 373
<212> TYPE: DNA
<213> ORGANISM: Homo sapiens

<400> SEQUENCE: 132

```
caggtgcagc tggtgcagtc tggggctgag gtgaagaagc ctgggtcctc ggtgaaggtc    60
tcctgcaagg cttctggagg catcttcatc agccaagcta tcagctgggt gcgacaggcc   120
cctggacaag ggcttgagtg gatgggaggg atcatcccta tgtttggtgc aactaactac   180
gcacagaagt tccagggcag agtcacgatt accgcggaca atccacgaa cacagtctac    240 atggagctga gcagcctgac atctgaggac acggccgtgt attactgtgc gagactcggt   300
tcggggagtt atcataacgg acccaactgg ttcgacccct ggggccaggg aaccctggtc   360
accgtctcct cag                                                      373
```

<210> SEQ ID NO 133
<211> LENGTH: 8
<212> TYPE: PRT
<213> ORGANISM: Homo sapiens

<400> SEQUENCE: 133

Gly Phe Thr Phe Ser Ser Tyr Ala
1               5

<210> SEQ ID NO 134
<211> LENGTH: 8
<212> TYPE: PRT
<213> ORGANISM: Homo sapiens

<400> SEQUENCE: 134

Ile Ser Tyr Asp Gly Ser Asn Gln
1               5

<210> SEQ ID NO 135
<211> LENGTH: 22
<212> TYPE: PRT
<213> ORGANISM: Homo sapiens

<400> SEQUENCE: 135

Ala Lys Asp Pro Arg Leu Arg His Leu Leu Tyr Phe Pro Phe Thr Ser
1               5                   10                  15

Met Ile Tyr Phe Asp Tyr
            20

<210> SEQ ID NO 136
<211> LENGTH: 24
<212> TYPE: DNA
<213> ORGANISM: Homo sapiens

<400> SEQUENCE: 136

```
ggattcacct tcagtagtta tgcc                                           24
```

<210> SEQ ID NO 137
<211> LENGTH: 24
<212> TYPE: DNA
<213> ORGANISM: Homo sapiens

<400> SEQUENCE: 137

```
atatcatatg atggaagtaa tcaa                                           24
```

<210> SEQ ID NO 138
<211> LENGTH: 66
<212> TYPE: DNA
<213> ORGANISM: Homo sapiens

<400> SEQUENCE: 138

```
gcgaaagacc cccgtcttag gcacctgcta tatttcccgt ttacatctat gatttacttt    60
```

```
gactac                                                              66

<210> SEQ ID NO 139
<211> LENGTH: 129
<212> TYPE: PRT
<213> ORGANISM: Homo sapiens

<400> SEQUENCE: 139

Gln Val Gln Leu Val Glu Ser Gly Gly Val Val Gln Pro Gly Arg
1               5                  10                  15

Ser Leu Arg Leu Ser Cys Ala Val Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Asp Pro Arg Leu Arg His Leu Leu Tyr Phe Pro Phe Thr Ser
            100                 105                 110

Met Ile Tyr Phe Asp Tyr Trp Gly Gln Gly Thr Leu Val Thr Val Ser
        115                 120                 125

Ser

<210> SEQ ID NO 140
<211> LENGTH: 388
<212> TYPE: DNA
<213> ORGANISM: Homo sapiens

<400> SEQUENCE: 140
caggtgcagc tggtggagtc tgggggaggc gtggtccagc ctgggaggtc cctgagactc       60
tcctgtgcag tctctggatt caccttcagt agttatgcca tgcactgggt ccgccaggct      120
ccaggcaagg ggctggagtg ggtggcagtt atatcatatg atggaagtaa tcaatattat      180
gcagactccg tgaagggccg attcaccatc tccagagaca attccaagaa cacactatat      240
ctgcaaatga acagcctgag agctgaggac acggctttgt attactgtgc gaaagacccc      300
cgtcttaggc acctgctata tttcccgttt acatctatga tttactttga ctactggggc      360
cagggaaccc tggtcaccgt ctcctcag                                         388
```